(12) United States Patent
Kimura

(10) Patent No.: US 9,261,472 B2
(45) Date of Patent: Feb. 16, 2016

(54) SPECIFIED GAS CONCENTRATION SENSOR

(75) Inventor: Mitsuteru Kimura, Miyagi (JP)

(73) Assignee: Tohoku Gakuin, Miyagi (JP)

( * ) Notice: Subject to any disclaimer, the term of this patent is extended or adjusted under 35 U.S.C. 154(b) by 167 days.

(21) Appl. No.: 13/821,805

(22) PCT Filed: Sep. 8, 2011

(86) PCT No.: PCT/JP2011/070427
§ 371 (c)(1),
(2), (4) Date: Apr. 25, 2013

(87) PCT Pub. No.: WO2012/033147
PCT Pub. Date: Mar. 15, 2012

(65) Prior Publication Data
US 2013/0209315 A1 Aug. 15, 2013

(30) Foreign Application Priority Data
Sep. 9, 2010 (JP) ................. 2010-202142

(51) Int. Cl.
*G01N 25/24* (2006.01)
*G01N 25/32* (2006.01)
*G01N 25/48* (2006.01)

(52) U.S. Cl.
CPC ........ *G01N 25/4873* (2013.01); *G01N 25/4826* (2013.01)

(58) Field of Classification Search
CPC ................ G01N 25/4873; G01N 25/4826
USPC .............. 73/23.2–31.08; 422/83–98
See application file for complete search history.

(56) References Cited

FOREIGN PATENT DOCUMENTS

JP 2008-111822 * 5/2008

OTHER PUBLICATIONS

Machine Translation of JP 2008-111822 pp. 1-20.*
Shin, Woosuck, et al. "Planar catalytic combustor film for thermoelectric hydrogen sensor." Sensors and Actuators B: Chemical 108.1 (2005): 455-460.*
Jasinski, Piotr, Toshio Suzuki, and Harlan U. Anderson. "Nanocrystalline undoped ceria oxygen sensor." Sensors and Actuators B: Chemical 95.1 (2003): 73-77.*

* cited by examiner

*Primary Examiner* — Lyle Alexander
*Assistant Examiner* — Robert Eom
(74) *Attorney, Agent, or Firm* — Young & Thompson

(57) ABSTRACT

A specified gas concentration sensor includes a thin film thermally separated from a substrate, which is provided by a heater, a temperature sensor and an absorbing substance of a specified gas, and temperature change accompanied by heat generation while absorbing the specified gas in an ambient gas being capable of measuring by the temperature sensor. The absorbed specified gas is released from the absorbing substance by heating with the heater, and after stopping heating with the heater, the specified gas concentration in the ambient gas is obtained by utilizing an output of the temperature sensor at a time passing a predetermined time which is a thermal time constant of the thin film or longer at which the specified gas is absent from the heater. An optional heat conductive type sensor having no absorbing substance of the specified gas can broaden the measurable range of the specified gas concentration.

23 Claims, 12 Drawing Sheets

SPECIFIED GAS CONCENTRATION SENSOR

TECHNICAL FIELD

The present invention relates to a concentration sensor of a specified gas such as a hydrogen gas or an oxygen gas, and to a specified gas concentration sensor for measuring a specified gas concentration in which an absorbing substance of the specified gas causes an exothermic reaction when it absorbs a hydrogen gas ($H_2$) or an oxygen gas ($O_2$) (in general, it is absorbed in an atomic state), while it causes an endothermic reaction when it releases the same, and in particular, a temperature rise based on the exothermic reaction at the time of absorbing the specified gas such as a hydrogen ($H_2$) gas or an oxygen ($O_2$) gas in an ambient gas is measured by a temperature sensor.

BACKGROUND ART

It has been known that there is a risk of explosion in an extremely broad range when a hydrogen gas exists in the air in an amount of 4.0 to 75.0% (% by volume). Accordingly, it is important to measure the hydrogen gas concentration in a low concentration at the lower explosion limit of 4.0% or less. Heretofore, as a gas sensor, there has been known a catalytic combustion type hydrogen gas-detection sensor (see Patent Document 1) in which the temperature of a catalyst such as tin oxide and Pt is raised by a heater and the catalytic action thereof is combined.

Also, as a semiconductor gas sensor, there has been known a sensor in which change in electric resistance is used by utilizing change in carrier density at the surface of the semiconductor due to adsorption of a reducing gas.

In addition, there was a sensor which has been heightened gas selectivity by utilizing absorption or permeation of a specified gas such as hydrogen. For example, as a device to detecting hydrogen by utilizing a hydrogen storage alloy, there has been known a hydrogen-detecting device (see Patent Document 2) which detects a hydrogen-absorption amount based on the size of the detected strain in which the hydrogen storage alloy is adhered to one surface of a substrate, and a strain gage is attached to the other surface, and the strain of the substrate caused by volume expansion of the hydrogen storage alloy when it absorbs the hydrogen is detected by the strain gage.

It has also been proposed a hydrogen detecting device (see Patent Document 3) for detecting a concentration of a hydrogen gas contained in a gas by utilizing a hydrogen storage alloy having high selectivity of hydrogen and detecting change in the state (weight change) when the hydrogen is absorbed while maintaining the hydrogen storage alloy to a constant temperature.

It has heretofore been known as an oxygen gas sensor that an oxygen concentration can be measured by making an oxygen (O) being absorbed (stored) (intercalation) to the interlaminar of titanium disulfide ($TiS_2$) which is a layered crystal and from the change in resistance at that time. In general, it has also been known that by spontaneously absorbing an atom (an oxygen atom in case of an oxygen gas) which constitutes a gas molecule, a temperature of the substance which absorbs the atom increases.

Heretofore, as a temperature sensor, there are an absolute temperature sensor which can measure the absolute temperature and a temperature difference sensor which can measure the temperature difference alone. As the absolute temperature sensor which can measure the absolute temperature, there are a thermistor, a transistor thermistor (Patent Document 4, JP Patent No. 3366590) which uses a transistor as a thermistor and a diode thermistor (Patent Document 5, JP Patent No. 3583704) which uses a diode as a thermistor, which are invented by the present applicant, and further an IC temperature sensor in which the temperature is in a linear relationship with a forward voltage of a diode or a voltage between emitter bases of a transistor. Moreover, as the temperature difference sensor which can measure the temperature difference alone, there have been a thermocouple and a thermopile in which the thermocouples are connected in series to increase output voltage.

It has heretofore been proposed a hydrogen sensor (Patent Document 6) which is constituted by a microcapsule means to encapsulate powder particles of a hydrogen storage alloy with a metal film, a temperature detecting means by a thermocouple, an integrating means in which the powder of the hydrogen storage alloy encapsulated by the microcapsule means and the thermocouple as the temperature detecting means are contained in a cap and an electronic controlling means by an electronic controlling portion including a power source as main characteristics.

The present inventor has also invented previously "a gas sensor element and a gas concentration measurement device using the same" (see Patent Document 7) and proposed a gas sensor element and a gas concentration measurement device which are intended to measure the concentration of a hydrogen gas in which one or a plural number of temperature sensors and a gas-absorbing substance which absorbs a gas to be detected are provided to a thin film thermally separated from a substrate, and the temperature sensors are so provided that temperature change accompanied by heat absorption or heat generation at the time of absorption or release of the gas to be detected. After that, he has conducted experiments and improvement thereof, and as a result, the best embodiments which conform to the various objects can be obtained as the present invention.

PRIOR ART DOCUMENTS

Patent Document

Patent Document 1: JP 2006-201100A
Patent Document 2: JP H10-73530A
Patent Document 3: JP 2005-249405A
Patent Document 4: JP Patent No. 3366590C
Patent Document 5: JP Patent No. 3583704C
Patent Document 6: JP 2004-233097A
Patent Document 7: JP 2008-111822A

SUMMARY OF THE INVENTION

Problems to be Solved by the Invention

In a hydrogen gas-detection sensor in a catalytic combustion type as shown in Patent Document 1, it is so constituted that burning is done at a relatively low temperature using a catalyst in which fine particles such as Pt are carried on an oxide under heating with a heater, and heat of reaction is utilized for detection, but selectivity of the gas is poor since it is reacted with a gas so long as it is a combustible gas. Moreover, it requires a temperature of 100° C. or higher even when it is said to be a low temperature using a catalyst, and the presence of oxygen in the air is indispensable since an action of combustion is utilized. In particular, a minute amount of a hydrogen gas concentration is to be measured during heating with the heater, it is necessary to control the heating temperature of the heater to be stable, and further a minute temperature rise is to be measured at high temperatures so that problems in the point of precision in the control circuit or the detection circuit are exposed. Also, it utilizes a catalytic reaction in order to deflagrate at a temperature as low as possible, and the surface state of the catalyst is important in the catalytic reaction but there are problems that the surface state of the catalyst has changed with a lapse of time by repeating heating and cooling for the purpose of making the surface porous or forming the catalyst by dispersing fine particles of platinum (Pt) in the oxide or catalytic properties has been changed due to change in the size of fine particles of platinum (Pt). Accordingly, it has been desired to provide a stable specified gas concentration sensor which can ignore the change with a lapse of time and which can operates at a low temperature without using a catalyst.

There has been also known a semiconductor gas sensor which utilizes gas adsorption at the surface of the semiconductor but there is a problem that it reacts with any material so long as it is a reducing gas, i.e., the problem of selectivity of the gas.

In a sensor which uses a hydrogen storage alloy and a hydrogen gas concentration is detected from the extent of strain at the time of absorbing hydrogen as shown in Patent Document 2, it is suitable for detecting a high concentration of hydrogen, but it is not suitable for detecting a wide range of gas concentrations from a low concentration to a high concentration, and further there is a problem of fatigue since it utilizes physical deformation.

In a sensor shown in Patent Document 3, it is necessary to incorporate a quartz resonator which is a detecting means for detecting change in the state (weight change) when the hydrogen is absorbed or a Peltier element which is a temperature controlling means to control the detecting element substantially the same temperature so that there are problems that the Peltier element consumes a large electric power and the sensor itself inevitably becomes a large-size.

In a sensor shown in Patent Document 6, it is necessary to have a microencapsulating means to encapsulate powder particles of the hydrogen storage alloy with a metal film, necessary to make the powder to regulate a diameter of about 20μ by the initial stage pulverization step after storing hydrogen to the hydrogen storage alloy, and necessary to have a step of enclosing the connected portions at the ends of the two kinds of metal wires constituting the thermocouple and powder of microcapsules of the hydrogen storage alloy in a cap, applying a pressure from around to clamp the cap made of a porous material through which the hydrogen gas can pass, and attaching it to the flame of the sensor to manufacture an integrated hydrogen sensor. Thus, it is not suitable for mass production and it is difficult to make a microminiaturization whereby its heat capacity is large and is a sensor which takes a time for detecting a hydrogen gas concentration of several minutes or longer. In addition, the hydrogen gas concentration is obtained by measuring a time until it is cooled under the predetermined temperature or lower after heating, so that the measurement time of the hydrogen gas concentration depends on the hydrogen gas concentration whereby, for example, it is impossible to measure within one second. In addition, the hydrogen storage alloy which is a LaNi series or MgTi series alloy comprising an eutectic mixture (eutectic material) by the used metals such as Cu, Ca, La, Mg, Ni and Ti is in a powder state so that uniform coating by a metal is difficult whereby there are problems that it reacts with a vapor to be oxidized and loses hydrogen storage properties and change with a lapse of time is remarkable.

Moreover, when the gas sensor element proposed by the present inventor shown in Patent Document 7 is used as a hydrogen concentration sensor which is to detect a hydrogen gas as a specified gas, the following problems are revealed as a result of various kinds of experiments until now. 1. When the hydrogen is absorbed by the absorbing substance of the hydrogen to become an equilibrium state, then, the exothermic reaction also stops so that increase in temperature also stops, 2. when a hydrogen gas is injected into an ambient gas, a time until stopping the temperature rise is markedly changed depending on the hydrogen gas concentration by completely absorbed by the absorbing substance of the hydrogen, in particular, when the hydrogen gas concentration is 5 to 10% (which is to show % by volume) or more, the temperature peak due to the exothermic reaction becomes large in proportion to the hydrogen gas concentration, but accompanied by the same, hydrogen is completely absorbed by the absorbing substance of the hydrogen within a short period of time to quit the exothermic reaction, and there is a problem that all the temperature rise is terminated within the thermal time constant $\tau$ which is a heat response time of the thin film at the detecting portion, whereas it depends on the heat capacity of the thin film 10 which is the detecting portion having the structure floating in the air, whereby measurement of the hydrogen concentration is difficult as it is and a specific device is required, 3. even when the hydrogen gas concentration is raised in the air, and the detecting portion provided by a substance absorbing the hydrogen is so heated with the same electric power that the temperature becomes one which is capable of starting burning of the hydrogen, the thermal conductivity of the hydrogen is the largest in the gases whereby heat dissipation at the detecting portion becomes significant and the temperature at the detecting portion rather becomes low and it is found that there is a temperature peak due to heat generation based on the burning of the hydrogen during heating with the heater at a certain hydrogen gas concentration (existence of a peak hydrogen gas concentration), 4. at the low hydrogen gas concentration in which the hydrogen gas concentration is 0.1% or so, a heat dissipation effect by increase in thermal conductivity due to hydrogen-containment is larger than the temperature rise from the room temperature based on combustion of hydrogen during heating with the heater, and after all, it is found a phenomenon that it is smaller than the temperature rise at the hydrogen gas concentration of 0% whereby it is reversed, and also found is that measurement of the hydrogen gas concentration is difficult otherwise any specific device is done in the region of an extremely low concentration of the hydrogen when the temperature rise by burning using heating with the heater at 100° C. or so is utilized by the catalytic effect such as Pt (platinum) by hydrogen-containment, 5. it is found that there exists a hydrogen concentration which becomes a peak of temperature rise with regard to the hydrogen gas concentration in the air concerning the temperature rise due to burning at the time of heating or the temperature rise due to exothermic reaction based on hydrogen absorption in the cooling procedure after stopping the heating. Accordingly, the hydrogen gas concentration cannot be determined only by the temperature rise due to heat generation and it is required to measure the temperature rise utilizing a different mechanism, etc.

FIG. 13 shows output characteristics at the time of heating with the heater in the region where the hydrogen gas concentration as the specified gas is large by using the specified gas concentration sensor element 100 which has the structure at the initial stage of the present invention produced experimentally with the structure shown in FIG. 16. An outline of the specified gas concentration sensor element 100 of the structure of FIG. 16 is as follows. A thin film 10a and a thin film 10b are formed by dividing the top portion of a thin film 10 comprising a cantilever shaped n type SOI layer formed by thermally separated and floated in the air from a substrate 1 into two portion, and a heater 25 comprising a nichrome thin film is formed at the common region 15 at the part near the root at which the thin film 10a and the thin film 10b are divided among the thin films 10. At the thin film 10a and the thin film 10b, a thermocouple 120 comprising a n type SOI layer 12 and a nickel thin film formed through a thermal oxide film 51 formed thereon are formed, respectively, whereby this is made a specified gas concentration sensor to measure the temperature difference between the thin film 10a and the thin film 10b. Incidentally, each thermocouple 120 commonly has the SOI layer 12 to make a common ohmic electrode 60a, which is capable of being wired through an electrode pad 70. When the common ohmic electrode 60a of the substrate 1 is made cold junction, hot junctions of the thin film 10a and the thin film 10b of each thermocouple 120 and the common region 15 are ohmic electrodes 60b, 61b and 62b, respectively. At the thin film 10a, an absorption substance 5 of hydrogen is formed and acts as a sensor for detection. Also, at the thin film 10b, an absorption substance 5 of hydrogen is not formed and it acts as a sensor for reference. The results of the experiment using the experimentally produced specified gas concentration sensor of the hydrogen gas are shown in FIG. 13, which is the case of the experiment where the hydrogen gas concentration of from 10% to 100% during the heating and cooling procedure when the thin film 2 is heated (the thin film 10a and the thin film 10b located at the tip thereof are heated as a matter of course) to 150° C. or so with the same electric power, and it shows the characteristics where the hydrogen gas concentration is relatively large. Incidentally, this experimentally produced thin film 10 (including the thin film 10a and the thin film 10b) is a cantilever shape, the size from the supporting portion of the substrate to the tip of the thin film 10a or the thin film 10b is a length of 5 millimeter (mm), and it has a slit 41 for thermal resistance at the neighbor of the supporting portion of the substrate to prevent from thermal conduction to the substrate and the thickness is a constant of 10 micrometer ($\mu$m) or so, which is an equal size provided at the tip portion of the thin film in parallel but it is a large sized shape since the thin film 10a and the thin film 10b are formed with wide width. Thus, the thermal time constant $\tau$ in the whole pure air of the thin film 2 is as large as 700 microseconds ($\mu$Sec) or so, so that it is a relatively slow response. When the length is made short, it has been known, of course, that the thermal time constant $\tau$ becomes small in proportion to the square of the length.

From FIG. 13 which is the experimental results, the experiment is carried out by heating with a heater by supplying a constant electric power so that it becomes 150° C. or so, but at the temperature with such a degree, it can be understood that the effect of increasing thermal conductivity of the hydrogen is large whereby raising the temperature becomes small whereas there is an exothermic reaction by combustion as the hydrogen gas concentration increases with the hydrogen gas concentration of 10% or higher. Incidentally, in the experimentally produced specified gas concentration sensor, no balance membrane is formed at the thin film 10b having no absorption substance 5, so that there is unbalance in heat conduction in some extent between the thin film 10a and the thin film 10b, and temperature rise in the thin film 10a is larger in pure air even when they are similarly heated. During heating, which is not shown in FIG. 13, it becomes a saturated output with the output voltage of 0.6V or so, and when the hydrogen gas concentration becomes 60% or higher, due to the effect of increasing thermal conductivity of the hydrogen, it can be understood that it becomes 0.55V at 60% and at 100%, it is further lowered to become 0.4V or so as can be seen from FIG. 13. Also, FIG. 14 shows the result of detecting an extremely low concentration of the hydrogen gas concentration at around 0.1% (1000 ppm) or so by using the same experimentally produced specified gas concentration sensor as in the data of FIG. 13, during heating with a heater, it can be understood that the output is exceeded in 0% which is pure air containing no hydrogen gas than the hydrogen gas concentration of 0.1% whereby they are reversed. This can be considered by the effect that the thermal conductivity of the hydrogen is large and it shows the limit of detecting hydrogen gas with a low concentration during heating. To the contrary, as shown in FIG. 15, after stopping heating with the heater (time t=8.0 seconds), at the time t=11.0 seconds which is four times or so of the thermal time constant $\tau$=700 millisecond, whereas the differential output at the hydrogen gas concentration of 0% is substantially 0 (zero) V, ideal positive output can be obtained at 0.1%. According to the zero method, it can be clarified that the detection method is extremely effective in which at the extremely low region of the hydrogen gas concentration with high precision, the hydrogen gas concentration at the time of about four times of the thermal time constant $\tau$ after stopping heating with a heater is detected by measuring temperature rise portion alone due to exothermic reaction based on absorption of the hydrogen using a temperature sensor, in particular, a temperature difference sensor of a thermocouple.

For measuring a specified gas concentration in an atmospheric gas by utilizing change in electric resistance at the intercalation to a layered substance such as a layered compound for a specified gas such as oxygen, etc., it is necessary to form an electrode which is ohmic joining to the layered substance, but it is generally difficult in many cases to measure true change in the resistance value based on intercalation. Thus, it has been demanded to develop a method which can measure the specified gas concentration such as an oxygen gas simply and easily.

The present invention has been done in view of the above-mentioned problems, which is in particular an improvement of the gas sensor of Patent Document 7 which is an invention by the present inventor by specifying the specified gas to be detected to a hydrogen gas or oxygen gas, which is to correspond not only to the hydrogen gas but also the specified gas such as an oxygen gas, and is to measure the specified gas concentration such as a hydrogen gas and an oxygen gas by utilizing temperature change based on the exothermic reaction at the time of absorbing (including storage or adsorption) of the specified gas. For the measurement of the concentration of the hydrogen gas, an absorption-exothermic reaction due to palladium (Pd) which absorbs hydrogen alone is utilized, and for the measurement of the concentration of the oxygen gas, heat generation based on intercalation of a layered substance such as a layered crystal, etc., is utilized. An object is to provide a specified gas concentration sensor which is a small-sized, operates at a low temperature, when the specified gas is a hydrogen gas, presence of oxygen, etc., is not necessarily required, which is mass-producible, and accordingly inexpensive, has high selectivity of the gas, high sensitivity and high precision, and which can be broaden the measurable concentration range of the hydrogen gas or the oxygen gas.

Means to Solve the Problems

In order to accomplish the above-mentioned object, the specified gas concentration sensor of one embodiment comprises a thin film 10 thermally separated from a substrate 1, which is provided by a heater 25, a temperature sensor 20 and an absorbing substance 5 of a specified gas, and temperature change accompanied by heat generation at the time of absorbing the specified gas in an ambient gas being capable of measuring by the temperature sensor 20, wherein the absorbed specified gas is released from the absorbing substance 5 by heating with the heater 25, and in the cooling procedure after stopping heating with the heater, at the time region in which cooling is substantially finished when the specified gas concentration is 0%, the matter that the specified gas once released from the absorbing substance 5 of the specified gas by heating is getting to be absorbed and temperature rise occurs based on the exothermic reaction at the time of absorbing the specified gas and a thermal time constant plays like it becomes large is utilized, the specified gas concentration in the ambient gas is obtained by utilizing an output of the temperature sensor 20 at a time passing a predetermined time exceeding at least a thermal time constant $\tau$ of the above thin film 10 or longer at which the specified gas is not present at the heater 25.

In general, a substance such as hydrogen (H) is absorbed at room temperature, it becomes an exothermic reaction. In the specified gas concentration sensor of the present invention, an absorbing substance 5 of a specified gas such as hydrogen and oxygen formed on the thin film (the thin film floating in the air) thermally separated from the substrate causes a minute temperature rising accompanied by heat generation at the time of absorbing the specified gas. At this time, the change is detected by a temperature sensor 20 with high sensitivity formed at the thin film which is floating in the air but as mentioned above, there are problems that the specified gas is absorbed by the absorbing substance to become an equilibrium state, then, the exothermic reaction stops so that increase in temperature also stops, further, a time until stopping the temperature rise is markedly changed depending on the specified gas concentration by completely absorbed by the absorbing substance, in particular, when the specified gas is hydrogen, if the hydrogen gas concentration is 5 to 10% (which is to show % by volume) or more, the temperature peak due to the exothermic reaction becomes large in proportion to the hydrogen gas concentration, but accompanied by the same, hydrogen is completely absorbed by the absorbing substance of the hydrogen within a short period of time to quit the exothermic reaction, and all the temperature rise is terminated within the thermal time constant $\tau$ which is a heat response time of the thin film of the detecting portion, whereas it depends on the heat capacity of the thin film at the detecting portion. Also, when the specified gas is hydrogen, even when the hydrogen gas concentration is raised in the air, and the detecting portion (sensing portion) equipped with an absorbing substance of the hydrogen is so heated with the same electric power that the temperature becomes one which is capable of starting burning of the hydrogen, the thermal conductivity of the hydrogen is the largest in the gases whereby heat dissipation at the detecting portion becomes significant and the temperature at the detecting portion rather becomes low and it is found that there is a maximum (peak) due to heat generation based on the burning of the hydrogen during heating with the heater at a certain hydrogen gas concentration.

Accordingly, in the case of the hydrogen, it is not to detect temperature rise due to the combustion heat by burning the hydrogen gas by heating with the heater at 100° C. or higher, but, with regard to the specified gases such as hydrogen and oxygen, during the cooling procedure after stopping heating with the heater or at the time region substantially terminating the cooling, the specified gas once released from the absorbing substance 5 of the specified gas by heating is getting to be absorbed and temperature rise occurs based on the exothermic reaction at the time of absorbing the specified gas, and by this reason, the temperature is gradually returned to a temperature (room temperature) of the original ambient gas as if the thermal time constant becomes large. In the pure air (the specified gas concentration of 0%) in which no specified gas is contained, there is no absorption of the specified gas even when the absorbing substance 5 of the specified gas is mounted to the thin film 10 thermally separated from the substrate 1, so that there is no reaction heat whereby it is cooled at the proper thermal time constant $\tau$. In general, at the time passing four times or so of the thermal time constant $\tau$, the thin film 10 is considered to be substantially completely cooled to return to the room temperature. Accordingly, the temperature rise $\Delta T$ from the room temperature of the thin film 10 on which the absorbing substance 5 of the specified gas has been mounted after passing a time of four times or so of the thermal time constant $\tau$ after stopping the heating can be considered to be the result of the exothermic reaction alone based on the specified gas absorption of the absorbing substance 5 of the specified gas.

The specified gas concentration sensor according to another embodiment of the present invention is the case where the specified gas is made a hydrogen gas.

When a hydrogen gas is used as the specified gas, it has characteristics which are never possessed by the other gas based on the fact that the hydrogen is the smallest element of the atomic radius. This is used for utilizing it as a hydrogen gas sensor having an extremely high selectivity by utilizing the properties that palladium (Pd), etc., can allow permeating only the hydrogen gas, when the specified gas concentration sensor is utilized as a hydrogen gas sensor.

The specified gas concentration sensor according to a further embodiment is the case where the absorbing substance 5 of hydrogen is made a substance containing platinum (Pt) or palladium (Pd) which is a chemically stable substance.

As a material for absorbing (including storing or adsorbing) hydrogen, there are a simple metal such as palladium (Pd) or platinum (Pt), and further nickel (Ni) and niobium (Nb), or a metal called as a hydrogen storage alloy which is an alloy, an organic substance and ceramics. When these materials absorb (including storage or adsorb) hydrogen, these reactions are generally exothermic, for example, the reaction heat of the hydrogen storage alloy of $LaNi_5$ is about 7 kcal per mole of the hydrogen which is a large value as about 0.048 kcal per 1 g of the hydrogen. To the contrary, when the metal hydride compound is heated to raise the temperature (at this time, endothermic reaction occurs), then, hydrogen is released to return to the original hydrogen storage alloy. Thus, it has been known that the absorbing substance 5 of the hydrogen reversely absorbs or releases the hydrogen whereby a large amount of heat balance accompanied thereby.

At the time of absorbing the hydrogen of the hydrogen gas ($H_2$) to the absorbing material, it is generally stored not in the state of a gas but in the state of a single atom of hydrogen. A desired absorbing substance of the hydrogen of the present invention is a material in which the surface of the absorbing substance of hydrogen is not easily oxidized or affected by vapor or moisture, which does not cause crack even when heating and cooling are repeated, or which does not deform. In the case of an alloy, compositional change at the time of preparation is markedly affect to the absorption amount or heat generation amount, and there are problems in a yield of the product or unification of the product based on the design, so that a chemically stable and inactive simple metal such as palladium (Pd) and platinum (Pt) is preferred in such a meaning.

When the absorbing substance 5 of the hydrogen is formed into a thin film state, it is convenient since it can be easily formed by sputtering or electron beam deposition, etc., the surface area contacting to the hydrogen gas becomes large, heat capacity is small and there is high-speed responsibility, a time until completing absorption of the hydrogen gas can be adjusted by controlling the thickness, and accordingly, a time of raising the temperature due to exothermic reaction after stopping the heating can be adjusted, and it may be a plane thin film not necessary to form a porous or fine particles.

The specified gas concentration sensor according to an additional embodiment is the case where the absorbing substance 5 is coated by a protective film so that a gas different from hydrogen which physically or chemically reacts with the absorbing substance 5 of the hydrogen is not directly contacted with the absorbing substance 5.

When the absorbing substance 5 of the hydrogen is palladium (Pd), for example, there is a case where slight exothermic reaction can be observed by reacting with vapor. Thus, to prevent from reacting the absorbing substance 5 of the hydrogen and a gas different from hydrogen which physically or chemically reacts therewith, it is preferred to cover the absorbing substance 5 with a protective film which is a film in which the hydrogen atom can permeate the material of a thin film since its radius is the smallest in all the atoms but others atom or molecules of the gas cannot permeate the same. Also, the protective film is preferably a hydrophobic substance. For example, a gold (Au) thin film is suitable. A thickness or porosity of the protective film is preferably so adjusted that the absorbing substance 5 of the hydrogen inside thereof is not directly contacted to vapor.

The specified gas concentration sensor according to another embodiment is to measure a temperature of the temperature sensor 20 by heating the heater 25 with a predetermined electric power, voltage or current, stopping the same and at a time passing a predetermined time exceeding at least the thermal time constant $\tau$ of the thin film 10 or longer during the cooling process, and the hydrogen gas concentration is to be obtained in the hydrogen gas concentration range of the peak hydrogen gas concentration or lower.

As mentioned above, it has been known that when a concentration of the hydrogen gas as the specified gas is raised in the air, there is the maximum (peak) at a certain hydrogen gas concentration due to heat generation based on the burning of the hydrogen during heating at the temperature capable of starting burning of the hydrogen due to the large heat conductivity of the hydrogen. It has also been found out that there is a hydrogen gas concentration at which the temperature of the temperature sensor 20 for measuring the temperature of the absorbing substance 5 of the hydrogen due to the exothermic reaction by absorption of the hydrogen to the absorbing substance 5 at a certain hydrogen gas concentration even when it is a cooling procedure after stopping the heating (in the following, the hydrogen gas concentration which gives the peak is called as "peak hydrogen gas concentration"). Accordingly, by measuring the temperature rise $\Delta T$ which is the difference between the room temperature which is a surrounding temperature and the temperature of the thin film 10 after passing the time of four times of the thermal time constant $\tau$ after stopping the heating at the hydrogen gas concentration which gives the peak ("peak hydrogen gas concentration"), the concentration of a hydrogen gas in the air can be measured based on the data for calibration with regard to the temperature rise $\Delta T$ and the concentration of the hydrogen gas obtained before the measurement. Thus, after passing a final time, the temperature rise $\Delta T$ becomes substantially zero, so that the output of the temperature sensor accompanied thereby is subjected to differential amplification with the room temperature, the hydrogen gas concentration can be measured with high precision by utilizing the zero method. Incidentally, the peak hydrogen gas concentration was the value of 5 to 10% or so by the experiment whereas which depends on the structure of the thin film 10 containing the shape of the absorbing substance 5 of the hydrogen and the heating temperature.

The thin film 10 floating in the air itself is formed into a cantilever shape or a bridge structure which supports both ends, and the absorbing substance 5 of the hydrogen is provided thereto. The thin film 10 floating in the air is divided so that it is projected to a cantilever shape from the beam (crossbeam) portion connecting with the substrate 1 for supporting the thin film 10, or further beyond the cavity, so as to support to the opposite side by a bridge structure, and the position at which the absorbing substance 5 of the hydrogen is provided is preferably set at the tip portion of the cantilever shape or around the center portion of the bridge structure. The cantilever or the bridge structure forming the absorbing substance 5 of the hydrogen is preferably so formed as to have thermal resistance by providing a slit, etc., to the substrate or the beam (crossbeam) portion for difficulty escaping the heat generated at the absorbing substance 5 of the hydrogen to the substrate 1 through the beam (crossbeam) portion. The heat generated at the absorbing substance 5 of the hydrogen becomes difficult to escape to the substrate or the beam (crossbeam) portion, and the formed thin film portion shows a large temperature rise even when it is a minute amount of generating heat. At the thin film 10, a heater 25 such as a joule heating, etc., is also formed whereby it is so constituted that the hydrogen absorbed by the absorbing substance 5 of the hydrogen can be released. In addition, a temperature sensor 20 is also formed to measure the temperature of the thin film 10, in particular, minor temperature at the time of absorbing the hydrogen by the absorbing substance 5 of the hydrogen or temperature change precisely. Accordingly, the temperature sensor is a high sensitivity and high precision gas sensor by providing the portion of the thin film 10 at which the absorbing substance 5 of the hydrogen is formed.

Measurement of the hydrogen gas concentration can be done with high sensitivity and high precision when a temperature rise $\Delta T$ from the room temperature is measured after a time lapsed about four times or so of the thermal time constant $\tau$ from stopping the heating of the thin film 10 on which the absorption substance 5 of the hydrogen is mounted since the zero method can be used as such. However, as mentioned above, when the temperature rise is made large by providing a slit to the substrate or the beam (crossbeam) portion to make the thermal resistance large, then, the thermal time constant $\tau$ of the thin film 10 becomes large in proportion to the above whereby the response rate as the specified gas concentration sensor is delayed as a result. In general, it has been known that the thermal time constant $\tau$ of the thin film 10 floating in the air is proportional to square of the length if the material is the same and the thickness is also the same. From this, it is important to obtain a high-speed response by making the length of the thin film 10 short. This means that even in the temperature difference detection during the procedure where hydrogen with the hydrogen gas concentration range below the hydrogen gas concentration (peak hydrogen gas concentration), at which the temperature of the above-mentioned temperature sensor 20 becomes a peak, is gradually absorbed by the absorbing substance 5 of the hydrogen in the cooling procedure, the time after passing four times of the thermal time constant $\tau$, after stopping the heating, becomes shorter as the thermal time constant $\tau$ of the thin film 10 becomes short.

However, since the absorption rate is not changed under the same hydrogen gas concentration, a large temperature difference can be obtained so that it gives the merit that the measurement becomes high sensitivity, high precision and high speed response. For example, the thermal time constant $\tau$ of the cantilever having a length of 200 micrometers (μm) or so produced by the SOI layer is 2 milliseconds or so in the air which may vary depending on the thickness, and even when it is measured with five times of $\tau$, it can be measured within 10 millisecond or so whereby it can be said to be a high speed response.

As the above-mentioned temperature sensor 20, a pn-junction diode or transistor which is capable of making IC and capable of making a thin film can be used. These can be treated like as a thermistor so that an absolute temperature can be measured and the temperature of the thin film can be measured with extremely high sensitivity. However, when a temperature difference sensor which is a thermocouple or a thermopile in which a cold junction is formed at the substrate 1, and a hot junction is formed at the region at which the absorbing substance 5 of the hydrogen is provided or a neighbor thereof is used, the temperature difference between room temperature and the absorbing substance 5 of the hydrogen can be essentially taken out as an output as such so that it is extremely convenient since difference amplification can be carried out as such and the zero method can be applied as such. These temperature sensors are small-sized and have mass-productivity so that they are inexpensive. Also, these temperature sensors can be also utilized as a micro heater by turning on electricity to carry out joule heating. In such a case, without providing a heater 25 independently, the temperature sensor 20 can be also used as a heater 25. Of course, the temperature sensor 20 and the heater 25 are formed separately, for example, and both are formed in a thermocouple structure and utilized.

For obtaining a hydrogen gas concentration in an ambient gas by utilizing an output of the above-mentioned temperature sensor at the time of passing the thermal time constant $\tau$ of the thin film 10 at which no hydrogen of the heater exists after stopping the heating by the heater 25, at the time of passing the thermal time constant $\tau$ after stopping the heating by the heater 25, there is a temperature about 1/2.718 (about ⅓) or so of the temperature at the time of stopping the heating by the heater 25 and the effect thereof remains. After passing the time of four or five times of the thermal time constant $\tau$, the remaining temperature (a temperature which is off from the room temperature) can be deemed to be zero, so that it is better to actually measure the hydrogen gas concentration after passing the time four to five times of the thermal time constant $\tau$ by using the zero method as such.

The hydrogen gas concentration in an ambient gas (not necessarily limited to an air) can be theoretically measured when a thin film (a reference sensor) for reference having no absorption substance 5 of the hydrogen is so prepared that it has the same thermal time constant as that of the sensor for detection of the thin film 10 having the absorption substance 5 of the hydrogen, both are simultaneously heated and the temperature difference between them is measured at any time (even when the time not passing the thermal time constant $\tau$ or so) after cooling period where heating with the heater is stopped. However, according to the experiment, it is extremely difficult to obtain completely the same cooling characteristics in an ambient gas in the state of no hydrogen is present, and it is judged that an error is substantially remarkable otherwise after passing the thermal time constant $\tau$ or longer during the cooling period after stopping the heating by the heater.

The specified gas concentration sensor according to a further embodiment is the case where the specified gas is made hydrogen. This is the case equipped with a specified gas concentration sensor as a thermal conductive type sensor in which, apart from the thin film 10, a thin film 11 is formed thermally separated from a substrate 1 and to which a heater 26 and a temperature sensor 21 are provided, but an absorbing substance 5 of hydrogen is not provided or even when it is provided, it is made inactive, the heater 26 is heated under a predetermined electric power, voltage or electric current, measurement of the temperature of the heater 26 during heating or the temperature immediately after stopping the heating to passing a predetermined time during cooling, or measurement of a lapsed time until the temperature becomes a predetermined one is carried out by using the temperature sensor 21, and the concentration of the hydrogen gas from at least 3% or more and up to 100% can be measured by utilizing an output or change in output of the temperature sensor 21 based on the difference in thermal conductivity depending on the hydrogen gas concentration in the ambient gas.

That is, the above-mentioned specified gas concentration sensor where the specified gas is made hydrogen comprises a thin film 10 provided with a heater 25, a temperature sensor 20 and an absorption substance 5 of the hydrogen, which has a mechanism that the concentration of the hydrogen gas substantially 10% or less is measured by absorbing the hydrogen gas to the absorbing substance of the hydrogen during the cooling procedure after heating, and the temperature rise based on the heat generation is measured to obtain a hydrogen gas concentration. But this specified gas concentration sensor uses a different mechanism from the above mechanism in combination, i.e., this is a specified gas concentration sensor in which a specified gas concentration sensor as the so-called heat conduction type sensor which utilizes the difference in heat dissipation depending on the hydrogen gas concentration of the heated thin film 11, and it can be detected the hydrogen gas concentration from 0% to 100% with a wide range.

Only by the hydrogen gas concentration due to measurements of temperature rise based on the combustion heat of the hydrogen gas by heating and temperature after passing a time of an inherent thermal time constant $\tau$ during the slow cooling procedure based on absorption of the hydrogen gas by the absorbing substance 5 of the hydrogen at the time of cooling after stopping the heating as mentioned above, there exists a peak (due to existence of the peak hydrogen gas concentration, it exists of the hydrogen gas concentration at around 5 to 10%) in the characteristics of the hydrogen gas concentration and the measured temperature around the absorbing substance 5 of the hydrogen due to large thermal conductivity of the hydrogen gas. Accordingly, there exists the same temperature rise at the both sides of the peak of the hydrogen gas concentrations, whereby it was impossible to identify the hydrogen gas concentration by the measurement only one time of the temperature rise after stopping the heating. Therefore, it was necessary to use a hydrogen gas concentration measurement method having a different mechanism such as the heat conduction type sensor in combination.

The hydrogen gas has the highest thermal conductivity among the gases, so that when the other as is mixed with the hydrogen gas, it has been known that the thermal time constant at the time of heating and cooling the thin film 11 floating in the air becomes large with such an extent since the thermal conductivity becomes small than that of the pure hydrogen gas (the hydrogen gas concentration of 100%). Accordingly, contrary to the above, when the hydrogen gas is to be mixed into pure air or an ambient gas such as a nitrogen gas and the exothermic reaction such as burning, etc., can be neglected, under the heating of the thin film 11 by the heater 26 under the same power supply, it has been known that the reaching temperature of the thin film 11 is lowered since heat dissipation from the thin film becomes large in proportion to the hydrogen gas concentration. Also, during the cooling procedure after the heating, heat dissipation from the thin film becomes large substantially in proportion to the hydrogen gas concentration so that it rapidly cools and the thermal time constant becomes small. Thus, since there is no exothermic reaction based on the absorption of the hydrogen gas by the absorbing substance 5 of the hydrogen at the thin film 11, a hydrogen gas concentration of 1% or more can be accurately measured by measuring the value of the saturation temperature during heating the thin film 11 by the heater 26 or a time passing a predetermined time during the cooling procedure after the heating or a time until reaching to a predetermined temperature, etc. However, in the range of the hydrogen gas concentration not more than the peak hydrogen gas concentration (5 to 10% or so), the hydrogen gas concentration can be accurately measured by measurement of the temperature at the time of cooling after passing a predetermined time immediately after stopping the heating, so that it is sufficient when the measurement of the hydrogen gas concentration of at least 3% or more can be carried out.

The specified gas concentration sensor according to an additional embodiment is the case where, for estimating a rough range of the hydrogen gas concentration in an ambient gas whether it is larger than or smaller than the peak hydrogen gas concentration or not, output information of the temperature sensor 20 based on burning of the hydrogen during heating with the heater 25 can be utilized by heating the heater 25 under the predetermined electric powder, voltage or electric current.

As mentioned above, there exists a peak hydrogen gas concentration of the hydrogen gas concentration during the cooling procedure after stopping the heating with the heater 25, so that it was found that the values of the hydrogen gas concentration before and after the peak became uncertain. Accordingly, the temperature rise of the thin film 10 based on burning of the hydrogen during the heating with the heater 25 is large and the sensitivity is also large, so that an intention is to use it for the judgment whether the hydrogen gas concentration is in the range larger than the peak hydrogen gas concentration or not or in the range smaller than the same or not by using the catalytic combustion type specified gas concentration sensor in combination, which is different in mechanism from the specified gas concentration sensors defined in other embodiments. Thus, it can be made utilizable for confirming the existence of the hydrogen gas or obtaining rough information of the hydrogen gas concentration by utilizing the large output of temperature rise due to burning of the hydrogen possessed by the catalytic combustion type specified gas concentration sensor.

The specified gas concentration sensor according to yet another embodiment is the case where the specified gas is made an oxygen gas.

The oxygen gas is different from the hydrogen gas in the atomic radius of oxygen, so that the specific properties of the hydrogen having the smallest atomic radius cannot be used. However, a reaction (intercalation reaction) of storing (absorbing) oxygen having a large activity in an interlayer such as a layered crystalline, etc., can be used.

The specified gas concentration sensor according to an additional embodiment is the case where a layered substance is contained as an absorbing substance 5 of the oxygen, and an exothermic reaction accompanied by an intercalation reaction of the oxygen at the layered substance is utilized.

In general, in the intercalation reaction of the oxygen at the layered substance such as a layered crystalline, it has been known that volume expansion of the layered substance, electric resistance or exothermic reaction occurs. Among these, with regard to the volume expansion, it can be measured by a strain gauge, etc., but there are problems of a method for forming the strain gauge, calibration due to change in circumferential temperature, and a problem of hysteresis. In the case of using the electric resistance, there are problems of ohmic contact, insulating high resistance in many cases and a battle with Johnson noise. It is advantageous to measure the temperature change accompanied by the exothermic reaction using a temperature difference sensor such as a thermocouple or a thermopile which is led to the present invention.

A layered substance such as a layered crystalline, etc., is suitable for the absorbing substance 5 of the oxygen, and among these, titanium disulfide crystalline is suitable for the intercalation reaction of the oxygen. The titanium disulfide crystalline spontaneously takes an oxygen atom in the interlayer of its layered structure at room temperature (oxygen storage), to be a thermally equilibrium state. At the time of the oxygen storage, an exothermic reaction occurs so that the temperature rise at this time is measured by a temperature difference sensor and the oxygen concentration in the ambient gas is calculated based on the calibration data which are co-related to the circumferential temperature provisionally provided. This manner is the same as the detection of temperature difference based on the exothermic reaction in the absorbing substance 5 of the hydrogen as the above-mentioned hydrogen gas sensor.

The specified gas concentration sensor according to another embodiment is the case where the thin film 10 is divided into at least two thin film 10a and thin film 10b, a heater 25 which can equally heat the thin film 10a and the thin film 10b is provided at the common region of the part near the root at which these thin film 10a and thin film 10b are divided, to the thin film 10a are provided a temperature sensor 20 and an absorbing substance 5 of the hydrogen, to the thin film 10b is provided a temperature sensor 21, and an absorbing substance 5 of the hydrogen is not provided or even when it is provided, it is made inactive, the thin film 10a is used as a sensor for detecting hydrogen, the thin film 10b is treated as a reference sensor, the temperature difference between the thin film 10a and the thin film 10b can be detected and the output information of the temperature difference can be utilized.

For example, the thin film 10 is formed in a cantilever shape and dividing into two thin film 10a and thin film 10b, to the one of the cantilever shaped thin film 10a are provided an absorption substance 5 of a specified gas and a temperature sensor 20 as a sensor for detecting the specified gas, another cantilever shaped thin film 10b is mainly used for comparison with the sensor for detection as a reference sensor, and to the thin film 10b is not provided an absorption substance 5 of the specified gas but the mass thereof is to be preferably made substantially the same as that of the thin film 10a as the sensor for detection. When the absorbing substance 5 of the specified gas is provided to the thin film 10b, and it is to be utilized as a reference sensor, it is necessary to constitute it not to contact with the specified gas by, for example, covering the specified gas-absorbing substance 5 with a film which does not react with the specified gas. When such a constitution is employed, even when the temperature sensor is an absolute temperature sensor, a film of the absorbing substance 5 of the specified gas of the sensor for detection exposed to the specified gas absorbs the specified gas to cause an exothermic reaction, so that the temperature change is compared to the temperature of the reference sensor whereby the content of the specified gas in the gas can be measured by utilizing the calibration curve previously prepared.

The specified gas concentration sensor according to a further embodiment is the case where the thin film 10a and the thin film 10b are substantially the same shape, and if necessary, to the thin film 10b is formed a substance having the same heat capacity as the absorbing substance 5 of the specified gas formed at the thin film 10a as a balance film 6 whereby the heat response in the ambient gas containing no specified gas is made the same.

This is the case where the thin film 10a and the thin film 10b are made the same shape so that the thin film 10b which does not have an absorbing substance 5 of the specified gas or even when it is provided but made inactive can be used as a reference sensor of the thin film 10a having the absorbing substance 5 of the specified gas, and if necessary, this is the case where a substance having the same heat capacity as that of the absorbing substance (5) of the specified gas is formed as a balance film 6 so as to have strictly the same thermal time constant $\tau$ in the ambient gas existing no specified gas. A heater 25 is provided at the common region of the part near the root at which the thin film 10a and the thin film 10b are divided, which can heat the thin film 10a and the thin film 10b simultaneously, and when no specified gas is present in the ambient gas such as air and a nitrogen gas, the temperature sensor 20 and the temperature sensor 21 each provided to the thin film 10a and the thin film 10b, respectively, become the same output by simultaneously heated when they are heated by the heater 25 which is common thereto, and the difference of outputs between these becomes zero. When a specified gas is present in the ambient gas, in particular, the specified gas is a combustible gas such as a hydrogen gas, the temperature of the thin film 10a equipped with the absorbing substance thereof becomes higher temperature than that of the thin film 10b since during heating with the heater, it generally burns to cause temperature rise in the presence of an oxygen gas when it became a certain temperature or higher. According to this heating, the specified gas absorbed by the absorbing substance 5 of the specified gas is released. Also, during the cooling procedure after stopping the heating, burning is terminated and cooling is started, and absorption of the specified gas occurs again. Due to the exothermic reaction accompanied thereby, the lower the specified gas concentration is, the slower the temperature rise occurs, but absorption of the specified gas to the absorbing substance reaches the saturation, the exothermic reaction also quits and the temperature finally returns to the original room temperature. During the cooling procedure, according to differential amplification of the output voltages of the temperature sensor 20 and the temperature sensor 21 formed on the thin film 10a and the thin film 10b, respectively, the specified gas concentration is to be obtained by utilizing the calibration data concerning the differential output and the specified gas concentration previously obtained.

If the thin film 10a and the thin film 10b have completely the same heat capacity, the specified gas concentration can be theoretically obtained easily at any time during the cooling procedure as such from the relationship between the differential amplification output and the specified gas concentration data. In general, there exists some difference in heat capacity or thermal conductivity in the thin film 10 so that the thermal time constant is different in many cases, whereby it has been found that the specified gas concentration can be done stably with good reproducibility when the specified gas concentration is obtained by utilizing the differential amplification output after passing the original thermal time constant $\tau$ or later. Incidentally, it can be found out from the experiment, when the specified gas is a hydrogen gas, if the concentration exceeds 5%, the effects reveal since the thermal conductivity of the hydrogen gas is large, and as the hydrogen gas concentration becomes large, the value of temperature rise reaches to the peak (existence of peak hydrogen gas concentration) even when the same heating with the heater, and thereafter, it is rather lowered. When the hydrogen gas concentration is to be measured only by measuring the hydrogen gas concentration during the cooling step after stopping the heating with the heater, this method is effective for the measurement of the hydrogen gas concentration of the peak hydrogen gas concentration (about 5 to 10%) or less while it depends on the structure or heat capacity of the thin film 10.

In the above-mentioned example, it is the case where the thin film 10 is so formed by dividing into cantilever shaped projected portions as the thin film 10a and the thin film 10b, but not cantilever shape, the thin film 10a and the thin film 10b are elongated to make a bridge structure. The temperature sensors 20 and 21 are equally formed at the portion near to the center of the bridge structure at which the temperature rise is the highest when the bridged-structure thin film 10 is heated, and the absorption substance 5 of the specified gas is formed at the portion near to the center of the bridged-structure thin film 10 of one of the thin film 10a, whereby the temperature sensor 20 is preferably so formed that it can measure the temperature of the absorption substance 5 of the specified gas.

The thin film 10b to which no absorption substance 5 of the specified gas is formed is different in mass of the absorbing substance 5 of the specified gas even when it is formed with the equal shape as the thin film 10a to which the absorbing substance 5 of the specified gas is formed. Further, when the absorbing substance 5 of the specified gas comprises a metal such as palladium Pd, the thermal conductivity of the thin film 10a itself is also different so that heat responses at the time of heating and cooling are different in the ambient gas existing no specified gas whereby it becomes difficult to handle the thin film 10b as a complete reference sensor. In this case, it is preferred that a balance film 6 comprising a material having the same heat capacity as that of the absorbing substance 5 of the specified gas is formed on the thin film 10b, so that the heat responses at the time of heating and cooling are substantially the same even in the ambient gas in which no specified gas is present. It is also important in this case that the balance film 6 is made equivalent to the absorbing substance 5 of the specified gas formed on the thin film 10a including thermal conductivity by controlling the thickness and surface area, etc. Of course, it may carry out a differential amplification of the temperature outputs of the thin film 10a and the thin film 10b in consideration with the fact that they are unbalanced from the beginning. This is because the thin film 10b is completely cooled and returned to room temperature when the time is passed four times or longer of the thermal time constant $\tau$ after stopping the heating, so that a thermocouple is used as the temperature sensor of the thin film 10b, its output voltage is zero which is no problem, and the reason for carrying out the differential amplification of the outputs of the thin film 10a and the thin film 10b is that it is necessary for measuring the specified gas concentration even when it is during the heating or in the cooling procedure immediately after stopping the heating.

The specified gas concentration sensor according to an additional embodiment is the case where the thin film 11 is formed separately from the above-mentioned thin film 10, which is thermally separated from the substrate 1, and made an equal shape of the above-mentioned thin film 10 while it does not have the absorbing substance 5 of the specified gas.

Here, the above-mentioned thin film 11 is formed independently from the above-mentioned thin film 10 so that the shape becomes somewhat large, but the design can be done in the state without any restriction whereby a specified gas concentration sensor as a heat conduction type sensor can be easily formed. As the temperature sensor, it may be an absolute temperature sensor such as a platinum resistor or a temperature difference sensor such as a thermocouple and a thermopile. Also, these temperature sensors are joule heated to use them as a heater. The temperature difference sensor can be of course used as a heater alone without using it as a temperature difference sensor.

Practically, the thin film 11 is not independently provided from the thin film 10 onto the substrate 1, but among the thin film 10a and the thin film 10b in which the thin film 10 is divided, the thin film 10b which does not have an absorbing substance 5 of the hydrogen or even when it is provided but made an inactive state by coating with an inactive film which does not permeate the hydrogen whereby the thin film 10b making it equivalent to the state substantially having no absorbing substance 5 of the hydrogen may be utilized as the thin film 11. In this case, the hydrogen gas sensor can be made a compact specified gas concentration sensor. However, to the thin film 10a is provided an absorbing substance 5 of the specified gas so that the thin film 10 is heated by the exothermic reaction based on absorption of the specified gas to the absorbing substance 5 of the specified gas whereby the effect causes a problem. Therefore, the temperature sensor 20 and the temperature sensor 21 provided to the thin film 10a and the thin film 10b, respectively, are made temperature difference sensor such as a thermocouple, etc., and a common junction (hot junction or cold junction) is formed at the common region of the part near the root at which these thin film 10a and thin film 10b are divided, and the respective temperatures of the thin film 10a and the thin film 10b or the temperature difference may be measured by using the above portion as a standard.

The specified gas concentration sensor according to yet another embodiment is the case where the above-mentioned temperature sensors 20 and 21 are made a temperature difference sensor. The temperature difference sensor may include a thermocouple and a thermopile. The temperature difference sensor is suitable, for example, for measuring a temperature difference from the temperature of the absolute temperature sensor formed on the substrate 1 as a standard.

The temperature sensor 20 to be provided to the thin film 10 to which the absorbing substance 5 of the specified gas such as hydrogen or oxygen is provided is preferably so constituted that it can detect temperature rise alone from the ambient gas based on the exothermic reaction of the absorbing substance 5 of the specified gas in the ambient gas such as air, etc. This is because the temperature sensor for detecting the temperature of the ambient gas and the temperature rise from the ambient gas temperature (room temperature) based on the exothermic reaction due to absorption of the specified gas by the absorbing substance 5 of the specified gas which is a gas to be detected are required to be detected. When the temperature sensor is an absolute temperature sensor, two temperature sensors are required one of which is a temperature sensor for measuring the temperature of the ambient gas and the other is a temperature sensor 20 for measuring the temperature rise from the ambient gas based on the exothermic reaction. Thus, the problems reveal that these two independently existing absolute temperature sensors change with a lapse of time and the temperature precision accompanied by the measurement at the temperature which is deviated from the temperature at the time of calibration becomes worse. Accordingly, it is confronted to the problem that an error accompanied by the above makes impossible to detect extremely slight temperature change.

In such a case, when a temperature difference detection sensor such as a thermocouple and a thermopile which can detect the temperature change alone based on the reaction of the absorbing substance 5 of the specified gas which is a gas to be detected is used, and when the hot junction is provided at, for example, the portion of the absorbing substance 5 of the specified gas, and the cold junction is provided at the portion of the temperature standard, for example, at the substrate 1 or the reference sensor, then, the temperature rise based on the exothermic reaction of absorbing the specified gas to the absorbing substance 5 of the specified gas can be detected with high sensitivity and high precision. That is, when no temperature rise accompanied by absorption of the specified gas to the absorbing substance 5 of the specified gas appears, the output powder becomes essentially zero, whereby the zero is as the standard (the zero standard method), accurate temperature detection, i.e., detection and measurement of the presence of the specified gas such as a hydrogen gas can be accomplished with high sensitivity and high precision.

The specified gas concentration sensor according to a different embodiment is the case where an electric current is flown to the temperature sensors 20 and 21 to utilize them also as the heaters 25 and 26.

The above has previously been stated, and here, even when the temperature sensors 20 and 21 are absolute temperature sensors such as platinum, a varistor, a diode and a transistor, or temperature difference sensors such as a thermocouple, etc., joule heating can be carried out. In this case, they can be used as the temperature sensor as well as the heater. Or else, by utilizing the fact that they can be produced by the same procedures as the necessary temperature sensor, they may be used not as the temperature sensor but as the heater whereby a compact and inexpensive specified gas concentration sensor can be provided.

The specified gas concentration sensor according to an alternative embodiment is the case where an absolute temperature sensor is provided at the substrate for the measurement of the temperature of the ambient gas.

An absorption amount to the absorbing substance 5 of the specified gas or a calorific value accompanied thereby depends on the temperature of the ambient gas. In general, as the temperature of the ambient gas is low, the absorption amount of the specified gas becomes large and the calorific value accompanied thereby is also large. Also, when the specified gas is, for example, a hydrogen gas, heat generation based on the catalytic combustion of the hydrogen gas occurs at 100° C. or so, and the temperature of the ambient gas is required to be detected. Accordingly, it is necessary to provide a temperature sensor for measuring the temperature of the ambient gas, but the substrate 1 is exposed to the ambient gas temperature for a long period of time, and when the above-mentioned temperature sensors 20 and 21 are made temperature difference sensors, they are used as the standard temperature in many cases by forming the cold junction to the substrate, so that it is suitable to provide an absolute temperature sensor for measuring the temperature of the ambient gas to the substrate 1. As the absolute temperature sensor, there are platinum, a varistor, a diode and a transistor as mentioned above.

The specified gas concentration sensor according to a different embodiment is the case where the substrate 1 is a semiconductor substrate, a thin film 10 or a thin film 11 are formed through a sacrificing layer which has been formed by overlaying upward of the substrate 1, the sacrificing layer is removed by etching to form a cavity, and, if necessary, an electronic circuit can be formed onto the substrate 1.

When a semiconductor substrate is used as the substrate 1, according to the matured semiconductor IC technology, various electronic circuits such as an OP amplifier, a memory circuit, an arithmetic circuit, a heater driving circuit and an indicating circuit can be formed thereon. When the substrate is processed three-dimensionally by MEMS technique utilizing an anisotropic etching technology to the substrate itself, there is a less space for forming these IC electronic circuits and the substrate tends to be a large-sized. Moreover, the anisotropic etching, etc., are carried out after forming the IC electronic circuits due to restriction of the preparation steps so that the case sometimes occurs where the wirings of the IC electronic circuits may not endure the chemicals for the anisotropic etching. In such a case, by using the sacrificing layer etching technology, as in the present invention, the thin layer 10 or the thin layer 11 which is thermally separated from the substrate is formed in the form of overlaying upward the substrate and a piled up shape with floating in the air, and the temperature sensors 20 and 21, a heater 25 and a thin film of the absorbing substance 5 of the specified gas are formed at the portion and the IC electronic circuit is formed on the substrate (for example, a singlecrystalline silicon substrate) existing at the lower portion thereof whereby the surface can be used efficiently and a compact specified gas concentration sensor can be provided. Also, the thin film 10 or the thin film 11 is formed by a polysilicon, insulation by an oxide film can be easily carried out, it can be formed like a thermocouple as the temperature difference sensor, and the temperature sensor can be utilized as the heater. Moreover, the absorbing substance 5 of the specified gas can be easily formed by sputtering palladium (Pd) or platinum (Pt) whereby these films can be easily formed by a dry process using well-known MEMS techniques.

The specified gas concentration sensor according to another embodiment is the case where the specified gas concentration sensor element is covered by a cap having a mesh structure whereby air stream is shut out, and if necessary, it is made in an explosion-proof type.

The specified gas concentration sensor is a heat conductive type sensor so that if there is an air stream, the air stream snatches the heat from the heater whereby accurate specified gas concentration cannot be measured. Accordingly, even when there is a slight air stream, by covering the specified gas concentration sensor element by a cap having a mesh structure to shut out the air stream, the same effect as in the case where the air stream has shut out can be obtained.

Also, when the specified gas is a combustible gas such as hydrogen, it catches fire by heating with a heater, and depending on the concentration, there is a risk of explosion. As a method to prevent the explosion, it has been known that the risk can be avoided by covering at least the heater portion with a metal mesh (which is made an explosion-proof type), etc. That is, a mesh structure such as a metal, etc., is suitable, and in the specified gas concentration sensor of the present invention, the temperature of the thin film floating in the air is measured so that the effect of the air stream is extremely avoided. Accordingly, while the air stream is shut out, the hydrogen gas is required to be reached to the detecting portion smoothly. For example, it has been known that there is a possibility of explosion with the hydrogen gas concentration in the air of a broad range of 4.0 to 75.0%. When the specified gas of the present invention is made hydrogen, the hydrogen gas is released from the absorbing substance 5 of the hydrogen by the heater 25 or heating with the heater as a heat conductive type sensor by the same, so that the measurement of the hydrogen gas concentration range is indispensable. For such a purpose, the cap with a mesh structure which becomes porous such as a metal is suitable for shut out the air stream. In the present invention, the cap having a mesh structure has both of a shut out effect of the air stream and establishment of explosion-proof.

The specified gas concentration sensor according to an alternative embodiment is the case where at least an electronic circuit is provided so that the above-mentioned heaters 25 and 26 are heated with a predetermined cycle, and the specified gas concentration in the ambient gas is to be measured.

Here, as the specified gas concentration sensor of the present invention, a specified gas concentration sensor which is modularized and equipped with an electronic circuit such as an amplification circuit, an arithmetic circuit and a memory circuit, whereby the heaters 25 and 26 are so heated by the predetermined cycle along with the predetermined program by occurrence of clock pulse or a transistor is contained. Moreover, it is also directed a specified gas concentration sensor in which the main body of the specified gas concentration sensor modularized is mounted and also a power source, an arithmetic circuit and an indicating circuit are mounted to also display the specified gas concentration. The electronic circuit may be provided to the substrate by employing a semiconductor substrate as the substrate, or may be provided near the specified gas concentration sensor element to be modularized. Incidentally, the predetermined cycle is not necessarily limited to a cycle with a constant period but may be any cycle which is repeated.

In the specified gas concentration sensor of the present invention, the absorption substance 5 of the specified gas is formed onto the thin film 10 floating in the air from the substrate, so that the thermal time constant $\tau$ as a response speed becomes a high-speed operation of several milliseconds while it depends on the size of the thin film 10. Accordingly, the absorption substance (5) of the specified gas is also in a thin film state so that the releasing procedure of the specified gas by heating with the heater is also quit with 10 milliseconds in this case. Also, in the case of the cooling procedure, it also quit with 10 milliseconds so that even when the heating and the cooling procedure are included, it is sufficient with 30 milliseconds or so, whereby it can be provided a specified gas concentration sensor with a high-speed operation that has never been obtained.

With regard to heating with the heater, the thin film 10 is heated to the predetermined steady temperature, and by using this temperature as a standard, the thin film 10 or the thin film 11 may be further heated with a heater with a periodically and predetermined cycle to the predetermined temperature. In any case, this is the case where the absorbing substance 5 of the specified gas formed to the specified gas concentration sensor is to be treated that it is heated from the room temperature which is the temperature of the ambient gas, or a certain predetermined temperature to a temperature by the predetermined electric power, heating is stopped and it is cooled, whereby the specified gas concentration is detected by measuring temperature change based on absorption and desorption procedure at the absorbing substance 5 of the specified gas at that time, in particular, measuring temperature rise, time variation of the temperature and equivalent variation of the thermal time constant accompanied thereby, etc. When the specified gas concentration is large, the temperature rise of the thin film 10 to which the absorbing substance 5 of the specified gas is formed becomes large since heat of the reaction of the absorbing substance 5 of the specified gas also generally becomes large even when heating with the heater is the same. However, when the specified gas is a hydrogen gas and the concentration is 10% or higher, it must be considered about the cooling effect by heat dissipation due to large thermal conductivity of the hydrogen gas. Also, when the specified gas gets into the inside of the absorbing substance 5 of the specified gas, desorption (release) of the specified gas becomes difficult even when heating with the heater is carried out, and the equivalent thermal time constant tends to look large.

Thus, the present invention is to expect an action which goes back to the initial state by heating the thin film 10 or additional heating of the same by the heater 25 to promote desorption of the specified gas from the absorbing substance 5 of the specified gas. Also, the room temperature which is the temperature of the ambient gas is different from each other depending on the circumference and each measurement, so that this temperature is required to be measured. Absorption of the specified gas including storage and adsorption is larger in a low temperature, but to make the initial state or initial conditions constant, the thin film 10 may be preferably and intentionally heated by the heater 25 at a temperature (e.g., 30° C.) slightly higher than the circumferential temperature of the place usually measured.

Effects of the Invention

In the specified gas concentration sensor of the present invention, to the thin film 10 thermally separated from the substrate are provided the temperature sensor 20 and the absorbing substance 5 of the specified gas which absorbs the specified gas, so that even when it is a minute amount of heat absorption at the time of absorbing the specified gas, temperature change becomes large, and a temperature sensor with high sensitivity and high precision is so provided that the temperature change can be measured whereby there is a merit that a specified gas concentration sensor having high sensitivity and high precision can be provided.

In the specified gas concentration sensor of the present invention, there are merits that the absorbing substance 5 of the specified gas can be formed to a thin film state so that the surface area contacting with the specified gas becomes large, heat capacity is small and high-speed responsibility can be done, the specified gas in the ambient gas is rapidly absorbed to and released from the absorbing substance 5 of the specified gas so that it becomes high-speed response. Also, the absorbing substance 5 of the specified gas is not necessarily required to be porous and may be plane whereby there is a merit that a specified gas concentration sensor with less change with a lapse of time can be provided.

In the specified gas concentration sensor of the present invention, temperature rise of the thin film 10 by the exothermic reaction heat based on absorption of the specified gas at the cooling procedure after releasing the specified gas from the absorbing substance 5 of the specified gas by heating with the heater can be measured after passing the predetermined time of the original thermal time constant τ or later (it is desirably four times or longer of τ) at the time of no specified gas is present, so that the zero method which can be extremely high precision can be applied whereby measurement of an extremely low concentration of the specified gas can be realized. In particular, when the specified gas is a hydrogen gas, at the "peak hydrogen gas concentration" (a region of 5 to 10% or so) or less, measurement of the concentration with high precision can be carried out.

In the specified gas concentration sensor of the present invention, the hydrogen gas as the specified gas is a gas having the largest thermal conductivity, and according to this effect, when the hydrogen concentration is substantially 10% or more, there is a phenomenon that the hydrogen concentration is large, the temperature rise becomes little even when it is burning under heating. Also, it has been found by the experiment that there is a phenomenon that, in the cooling procedure or after completion of cooling, the absorbing substance 5 of the hydrogen causes temperature rise of the thin film 10 due to exothermic reaction heat by absorbing the hydrogen, and absorption is finished soon so that the exothermic reaction stops and the film is cooled again, there is a "peak hydrogen gas concentration" where a temperature rise of the absorption substance 5 of the hydrogen has a peak at a certain hydrogen gas concentration due to the effect of difference in the absorption rate depending on the hydrogen concentration. A heat conduction type specified gas concentration sensor for measuring a wide range of the hydrogen gas concentration including the "peak hydrogen gas concentration" can be used in combination so that there is a merit that a wide range of the hydrogen gas concentration from 0% to 100% can be measured with high precision.

In the specified gas concentration sensor of the present invention, when the heater 25, the absorbing substance 5 of the specified gas and the temperature sensor 20 are formed to the cantilever shaped thin film 10, the temperature sensor can be formed at the tip portion of the thin film 10 at which the temperature change is the most significant. Accordingly, there is a merit that a high sensitivity specified gas concentration sensor can be provided. In particular, when a sensor which can detect temperature difference alone such as a thermopile or a thermocouple is used as the temperature sensor 20, there is a merit that a reference sensor to which no absorbing substance 5 of the specified gas is formed is not necessarily required and the specified gas concentration can be measured only by using a cantilever shaped thin film 10 to which the absorbing substance 5 of the specified gas and the temperature sensor are formed and the temperature at which no specified gas is present as a standard. Incidentally, at this time, there is a merit that, as a heater 25, the temperature sensor 20 is subjected to joule heating to utilize it as a heater as well as a temperature sensor. In particular, when a thermocouple is used as the temperature sensor 20, this is used as the heater 25 and heated, and then, in the cooling procedure, the temperature sensor is utilized as the temperature difference sensor so that the zero method can be applied thereto as such whereby it is convenient.

In the specified gas concentration sensor of the present invention, when the heater 25, the absorbing substance 5 of the specified gas and the temperature sensor 20 are formed to the bridged structure thin film 10, there are merit that wiring, etc., to the substrate can be drawn from the both ends of the bridged structure, so that crowding of the wiring and electrical separation can be easily carried out, and the thermal time constant becomes small so that high speed response can be realized and the strength of the thin film 10 can be easily heightened.

In the specified gas concentration sensor of the present invention, the thin film 10 can be divided into two thin films having the equal shape, and to one thin film 10a are provided the absorbing substance 5 of the specified gas and the temperature sensor 20 for use as a detection sensor, and to the other thin film 10b is provided the temperature sensor 21, and if necessary, a balance film is also provided for use as a reference sensor. The thin film 10 is heated to the predetermined temperature with the heater 25 mounted to the common region of these two thin films, so that there is a merit that the temperature rise accompanied by the heat absorption of the specified gas at the absorbing substance 5 of the specified gas is subjected to differential amplification whereby the specified gas concentration can be measured by using the zero method with high sensitivity, high precision and easily.

The specified gas concentration sensor of the present invention uses the absorbing substance 5 (for example, as the specified gas, Pd in the case of the hydrogen gas and titanium disulfide in the oxygen gas) of the specified gas which can absorb or store the specified gas alone, so that there is an extremely high selectivity to the other gas.

In the specified gas concentration sensor of the present invention, when the specified gas is made a hydrogen gas, the hydrogen gas concentration in an ambient gas containing no general oxygen, for example, in a nitrogen gas, an argon gas or a methane gas, can be measured with high sensitivity and high precision without requiring the presence of a specified gas such as oxygen like a catalytic combustion type gas sensor, and it can be compact and capable of being portable so that it can be provided as a small sized hydrogen gas concentration meter by mounting an electronic circuit. In addition, when a noble metal such as Pd and Pt is used as the absorption substance 5 of the hydrogen, there is a merit that change with a lapse of time is extremely little since they are chemically stable and not oxidized so that a hydrogen gas concentration sensor having high reliability can be provided.

In the specified gas concentration sensor of the present invention, an absolute temperature sensor is always exposed to the ambient gas and provided to the substrate the temperature of which is substantially the same temperature as the room temperature which is the temperature of the ambient gas, so that the temperature of the substrate can be utilized as the room temperature which is the standard temperature. In particular, when the temperature difference sensor such as a thermocouple, etc., is used as the temperature sensor, the substrate can be utilized as the standard temperature of the cold junction, and the temperature rise alone from the temperature can be accurately measured. Also, an amount or a rate of the specified gas to be absorbed to the absorbing substance 5 is affected by the temperature of the ambient gas so that the measured value of the standard temperature is necessary for the correction in the measurement of the specified gas concentration, and by utilizing the measured value of the standard temperature, a high precision specified gas concentration sensor can be provided. In particular, when the substrate is formed by a semiconductor, there is a merit that the temperature sensor for a diode or other semiconductor can be formed by the matured IC technology.

In the specified gas concentration sensor of the present invention, the thin film 10 floating in the air is heated by a thin film heater 25 mounted thereon, so that there is a merit that heating and cooling can be carried out with a low electric power consumption and a high speed, and a thin film state absorption substance 5 of the specified gas is used so that complete release of the specified gas by heating is easy and can be carried out with a high speed.

In the specified gas concentration sensor of the present invention, a semiconductor substrate is used as the substrate 1, and the thin film 10 and the thin film 11 formed through a sacrificed layer formed overlaying upward of the substrate can be used. The sacrificed layer is removed by etching to form a cavity, and if necessary, an electronic circuit can be formed on the substrate 1, so that there is a merit that the electronic circuit can be effectively formed even when in the small semiconductor substrate and a compact specified gas concentration sensor can be provided.

In the specified gas concentration sensor of the present invention, there is a merit that the specified gas concentration sensor element can be formed, for example in a small size with 1 mm square or so, and mass-producible by the MEMS technology so that by attaching an extremely small sized cap with a mesh structure and porous to shut out the air stream whereby an explosion-proof type inexpensive specified gas concentration sensor can be provided.

EXPLANATION OF REFERENCES

Figure 1:
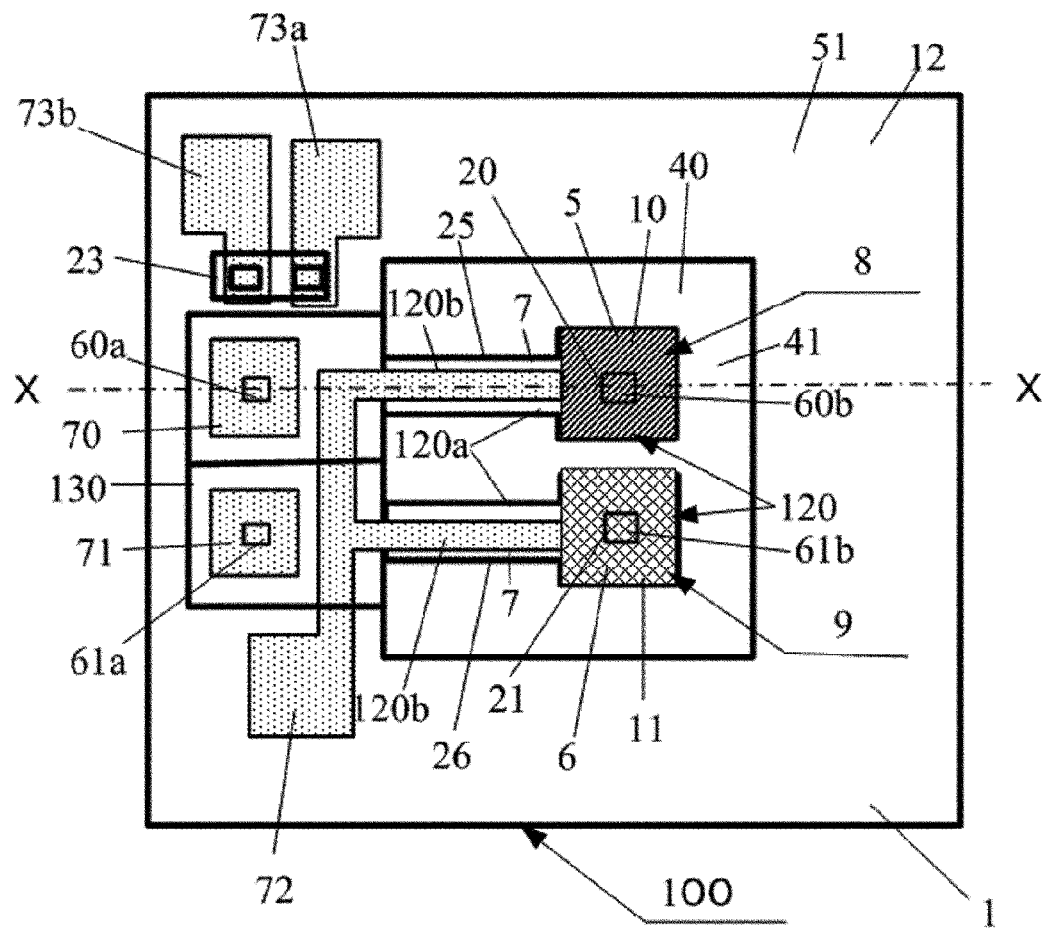
FIG. 1 This illustrates a schematic drawing of a plan view showing one example of the specified gas concentration sensor element 100 which is the characteristic feature of the specified gas concentration sensor of the present invention. (Example 1)

1: Substrate
3: Bridge structure
5: Absorbing substance
6: Balance film
7: Cantilever
8: Detection sensor
9: Reference sensor
10, 10a, 10b: Thin films
11: Thin film
12: SOI layer
13: BOX layer
15: Common region
18: Crossbeam
20, 21: Temperature sensor
23: Absolute temperature sensor
25, 26: Heaters
40: Cavity
41: Slit
50: Electric insulating film
51: Silicon oxide film
60, 60a, 60b: Ohmic electrodes
61a, 61b: Ohmic electrodes
62a, 62b: Ohmic electrodes
70, 71, 71a, 71b: Electrode pads
72, 72a, 72b: Electrode pads
73a, 73b: Electrode pads
74, 74a, 74b: Electrode pads
100: Specified gas concentration sensor element
110: Wiring
120: Thermocouple
120a, 120b: Thermocouple conductor
130: Groove
200: Cap
210: Mesh structure portion
300: Lead
310: Lead connected portion
350: Lead holder
360: Anchor portion
400: Gap
500: Element holder
600: IC electronic circuit

EMBODIMENT TO CARRY OUT THE INVENTION

The specified gas concentration sensor element which becomes the basis of the specified gas concentration sensor of the present invention can be formed by a silicon (Si) substrate which can form an IC thereon by using a matured semiconductor integrating technology and MEMS technology. With regard to the case where the specified gas concentration sensor element is prepared by using a silicon (Si) substrate, it will be explained in more detail in the following based on Examples by referring to the drawings. Also, when the specified gas concentration sensor of the present invention is modularized or the specified gas concentration sensor is utilized as a specified gas concentration meter utilizing the module will be explained by using the block diagram.

EXAMPLE 1

Figure 2:
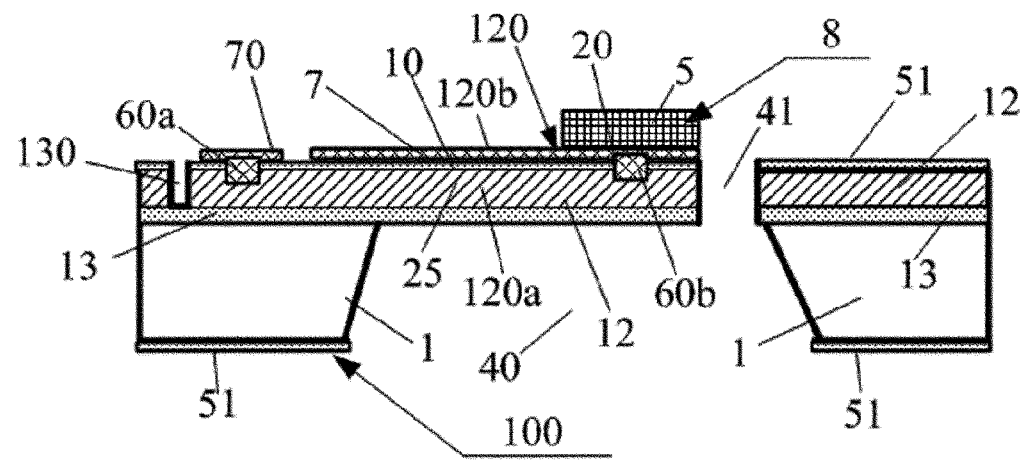
FIG. 2 This illustrates a schematic drawing of a cross-sectional view at X-X line of FIG. 1. (Example 1)

FIG. 1 is the case where a specified gas such as a hydrogen gas and an oxygen gas is to be detected in the specified gas concentration sensor of the present invention, which illustrates a schematic drawing of a plan view showing one example of a chip shaped specified gas concentration sensor element 100 prepared by utilizing a silicon singlecrystalline, and FIG. 2 is a schematic drawing of a cross-sectional view of the X-X cross-section thereof. Here, this is the case practiced by using an SOI substrate as a substrate 1, and one thin film 10 which is in the structure of floating in the air for heat separation from the substrate and a thin film 11 which is another thin film are cantilever states from the substrate 1 and the shapes are formed to be the same. To the thin film 10 are provided a heater 25, a temperature sensor 20 and an absorbing substance 5 of the specified gas, which acts as a detection sensor, and to the other thin film 11 are formed a heater 26, a temperature sensor 21 and a balance film in place of the absorbing substance 5 of the specified gas, which has been so adjusted that it becomes substantially the same thermal time constant τ in an ambient gas containing no specified gas and moved as a reference sensor. For example, when a hydrogen gas is to be detected as the specified gas, palladium (Pd) is formed as the thin film which is the absorbing substance 5 of the hydrogen, and when an oxygen gas is to be detected, a layered crystalline thin film of titanium disulfide is formed as the absorbing substance 5 of the oxygen gas. When the other gas is to be measured, it is of course formed a thin film of the absorbing substance having good selectivity to the specified gas by utilizing an intercalation effect, etc.

In this example, the heater 25 and the heater 26 are each provided by the temperature sensor 20 and the temperature sensor 21, respectively, which have both of the functions of a heater and a temperature sensor, and by passing an electric current to these temperature sensors to carry out joule heating to be capable of heating to 150° C. or so. Thereafter, in the cooling procedure after stopping heating with the heater, these are utilized with temperature sensors as the original functions. The temperature sensors 20 and 21 may be absolute temperature sensors such as platinum resistance and pn-junction diode, but here is the case where a temperature difference sensor as a thermo-couple 120 which can utilize the zero method as such is used, and measurement of the hydrogen gas concentration with high precision can be realized. These thermocouples 120 use an n-type SOI layer 21 as a thermocouple conductor 120a, and a metal film such as nichrome formed through a silicon oxide film 51 thereon is formed as a thermocouple conductor 120b. The standard temperature of the temperature difference sensor is made that of the substrate 1 which is considered to be the same as the room temperature which is the temperature of the ambient gas, and to the substrate are provided electrode pads 70, 71 and 72 of the thermocouple 120 so that they become the cold junction of the thermocouple 120 which is the temperature difference sensor. Also, this is an example in which an absolute temperature sensor 23 is formed to the substrate for measuring the temperature of the substrate 1 which provides the standard temperature. In this case, the absolute temperature sensor 23 is a pn-junction diode.

The operation of the specified gas concentration sensor is explained below when a hydrogen gas is used as the specified gas. When the lengths of the thin film 10 and the thin film 11 are each 300 micrometer (μm) or so, and the thickness of the SOI layer is 10 μm or so, then, the thermal time constant τ of the cantilever shaped thin film 10 and the thin film 11 become 5 milliseconds (mSec) or so. Also, when the SOI layer is an n-type and utilizes a specific resistance of 0.01 Ωcm or so, the resistance value of the thermocouple 120 is 30Ω or so and it is heated to 200° C. or so with an electric power for heating of 100 milliwatt or so. First, in an ambient gas containing a hydrogen gas ($H_2$ gas), for example, in the air, the thin film 10 and the thin film 11 are simultaneously heated. The terminals at this time are to apply voltage to an electrode pad 72 which is common thereto and between electrode pads 70 and 71 of the respective SOI layers 12 to act the temperature sensors 20 and 21 as heaters to raise the temperature from room temperature to 150° C. or so to release the hydrogen absorbed by the absorbing substance 5 of the hydrogen.

Next, an applied voltage for heating is made zero to stop the heating with the heater and the voltage between the electrode pad 70 and the electrode pad 71 is measured whereby the difference in the output voltage between the temperature sensor 20 and the temperature sensor 21 is measured by a differential amplification circuit. Fundamentally, if the thin film 10 and the thin film 11 are completely the same in thermally and electrically, the voltage between the electrode pad 70 and the electrode pad 71 is always zero when no hydrogen gas is present, but there is actually some difference and not become zero completely. After stopping the heating, at the time of four to five times or so of the thermal time constant τ, an output voltage (voltage between the electrode pads 70 and 71) of the thin film 11 having no absorbing substance 5 of the hydrogen becomes zero, but in the thin film 10, it has the absorbing substance 5 of the hydrogen so that temperature rise due to the exothermic reaction can be observed until absorption has completely finished due to the exothermic reaction based on absorption of the hydrogen gas at the time of cooling, and an output voltage between the electrode pads 70 and 71 can be observed. This value can be observed as a monotonous function in the range of a low hydrogen gas concentration lower than the above-mentioned peak hydrogen gas concentration, whereby the hydrogen gas concentration can be obtained by utilizing correlation data (calibration data) between the hydrogen gas concentration in the ambient gas at the time of passing a specific time after stopping the heating and an output voltage which had been prepared previously. In this case, when the hydrogen gas concentration is 0%, the output voltage between the electrode pads 70 and 71 essentially becomes zero at the time of four to five times or so of the thermal time constant τ after stopping the heating and the zero method can be applied, whereby it is particularly suitable for measuring the hydrogen gas concentration at the low hydrogen gas concentration region.

In the previous example, differential operation of the thin film 10 and the thin film 11 is carried out, and in the case where the hydrogen gas concentration has been known to be the peak hydrogen gas concentration or less, the thin film 11 for the reference sensor is not necessarily required. In such a case, only the thin film 10 having the absorbing substance 5 of the hydrogen is heated by a predetermined electric power, and after releasing the hydrogen, the output voltage between the electrode pad 70 and the electrode pad 71 is measured with the terminal voltage of the temperature sensor 20 which is a temperature difference sensor provided to the thin film 10. The hydrogen gas concentration can be obtained by utilizing the correlation data of the hydrogen gas concentration and the output voltage. In this case, of course, when no hydrogen gas is present, the output voltage becomes essentially zero so that the zero method can be applied as such whereby it becomes a specified gas concentration sensor with high precision.

However, there exists the above-mentioned peak hydrogen gas concentration, so that the thin film 10 and the thin film 11 are simultaneously heated, and the reached temperature of the thin film 11 immediately after stopping the heating is measured with the output voltage between the electrode pad 70 and the electrode pad 71. The correlation data of the hydrogen gas concentration at this stage and the reached temperature when the film is heated by the predetermined electric power have previously been obtained, and the thin films are treated as the heat conduction type hydrogen sensor whereby the hydrogen gas concentration with a wide range in the ambient gas can be obtained by comparing with the correlation data.

During the heating time, there is release of the hydrogen gas from the absorbing substance 5 of the hydrogen and temperature rise due to catalytic combustion, and the heating period is to be determined to a predetermined time, under such a condition, it is necessary to obtain correlation data (calibration data) between the hydrogen gas concentration and the reached temperature heated by the predetermined electric power previously. When the heating time is set to several times of the thermal time constant τ, e.g., four to five times thereof, then, the data which are stable and having good reproducibility can be obtained. Also, the output information concerning temperature rise based on burning of the hydrogen gas when heating is carried out can be utilized as confirmation information at the concentration region larger than and lower than the peak hydrogen gas concentration of the hydrogen gas.

When the outline of the forming process for processing the substrate 1 in the specified gas concentration sensor of the present invention shown in FIG. 1 and FIG. 2 are explained, it is as follows. When the n-type is used as the SOI layer 12 of the substrate 1, a thermocouple 120 is used as the temperature sensors 20 and 21, and the heater 25, so that an n-type thermal diffusion region is preferably formed at the portions of the ohmic electrodes 60a, 60b, 61a and 61b to obtain good ohmic contact by the conventionally known semiconductor fine processing technology. Also, as the absolute temperature sensor 23 provided to the substrate 1, a pn-junction diode is formed and it can be easily formed by the conventionally known diffusion technology.

As the thermocouple conductor 120b of the thermo-couple 120, it is necessary to make the material with the same metal since differential amplification is carried out. A metal of nichrome or nickel (Ni) has durability to the strong alkaline etchant so that it is suitable. When it is not exposed to the strong alkaline etchant but by dry etching, by using an aluminum (Al) series metal, an ohmic electrode, a wiring 110 and an electrode pad may be formed by the sputtering thin-film formation and photolithography. For patterning with Pd as the absorbing substance of the hydrogen, there is a special etchant, and dry etching is carried out, if necessary. A cavity 40 to be formed to the substrate 1 can be formed from the back surface by an etchant or DRIE, and a slit 41 from the front surface side is similarly formed to penetrate the substrate. Incidentally, the electrode pad 70 and the electrode pad 71 which becomes the terminal at the n-type SOI layer 12 side which becomes the cold junction at the substrate side of the thermocouple 120 formed to the thin film 10 and the thin film 11 are electrically separated by remaining in an island shape with a groove 130 which reaches to a BOX layer 13 not to short-circuited by the common n-type SOI layer 12.

The details of the above-mentioned Example 1 are the case where the specified gas is a hydrogen gas, and for example, when the specified gas is an oxygen gas, by utilizing an intercalation effect of titanium disulfide which stores (absorbs) the oxygen selectively, a titanium disulfide thin film which is a layered crystalline is formed with a thickness of 1 µm or so as the absorbing substance 5 for utilizing the exothermic reaction when the oxygen is stored (absorbed). For forming the titanium disulfide layered crystalline thin film, a thin film is formed by the conventionally known CVD (chemical vapor deposition method), sol-gel method or sputtering, and then, for controlling evaporation of the sulfur (S), for example, it is preferably subjected to heat treatment in hydrogen sulfide to carry out polycrystallization or single-crystallization to make a layered crystalline thin film. In the case of the oxygen gas, different from the hydrogen gas, its thermal conductivity is substantially the same as the air and the presence of the peak concentration as in the case of the hydrogen gas seems to be not admitted so that it is not necessary to distinguish a specific peak hydrogen gas concentration or less or more as in the hydrogen gas, and the exothermic reaction simply increases based on the concentration of 0 to 100%. Thus, oxygen is to be simply released from the absorbing substance 5 of the oxygen stored by heating, and the temperature rise from the circumferential temperature at the time of several times (for example, 4τ) of the thermal time constant τ at which no oxygen is present at the cantilever on which the absorbing substance 5 of the oxygen is mounted in the cooling procedure after stopping the heating is measured with the output voltage difference between the temperature sensor 20 and the temperature sensor 21 of the thermocouple 120 which is a temperature difference sensor, whereby the oxygen gas concentration can be measured.

EXAMPLE 2

Figure 3:
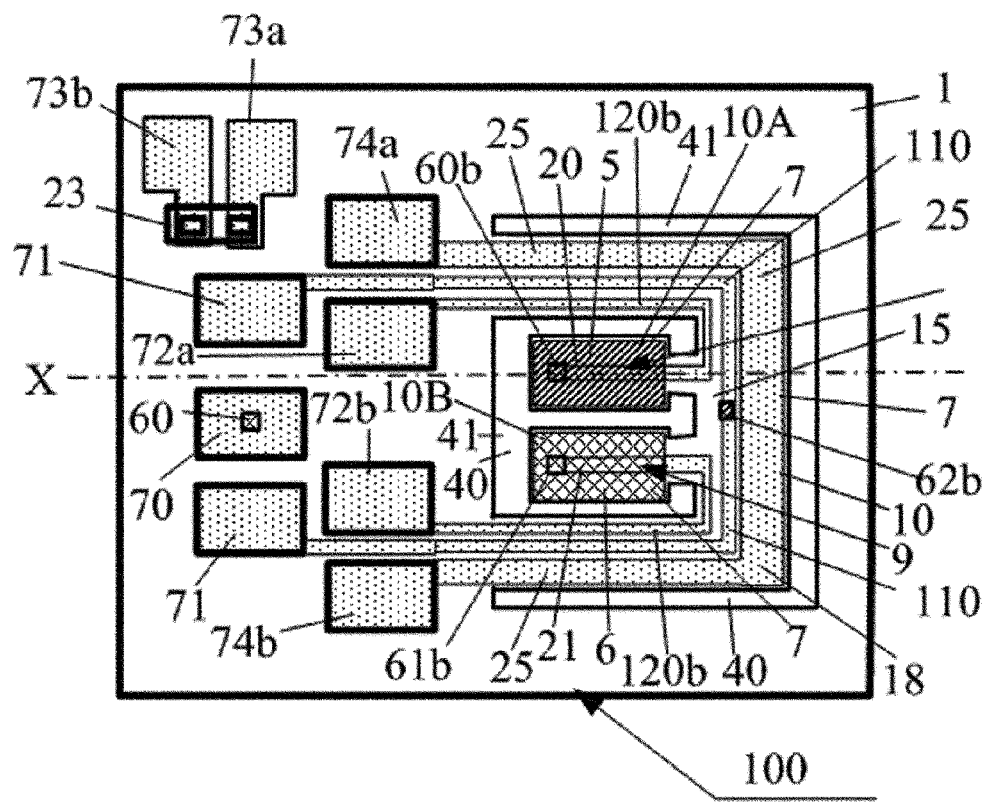
FIG. 3 This illustrates a schematic drawing of a plan view showing other example of the specified gas concentration sensor element 100 portion which is the characteristic feature of the specified gas concentration sensor of the present invention. (Example 2)
Figure 4:
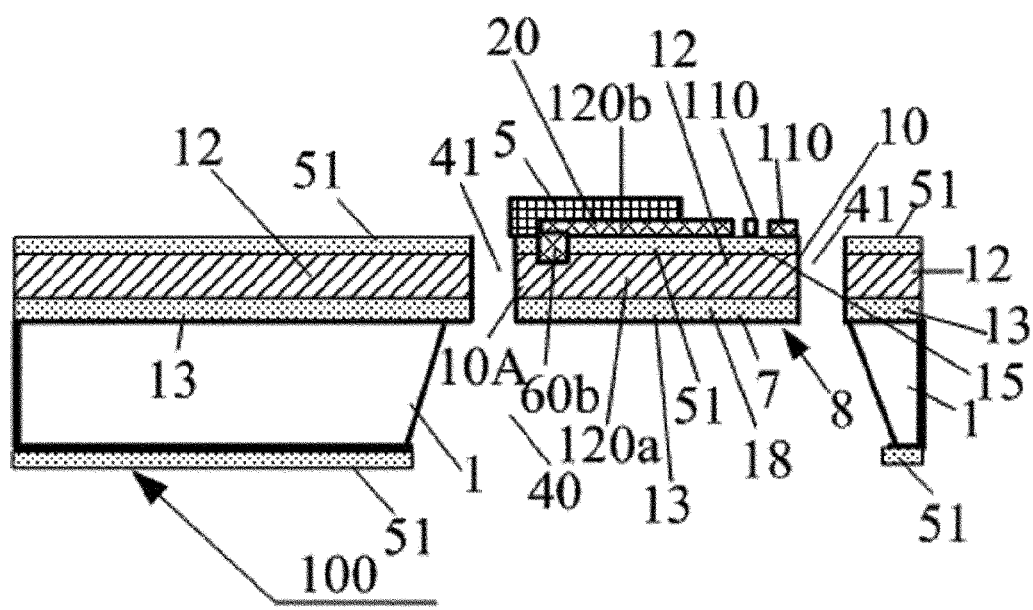
FIG. 4 This illustrates a schematic drawing of a cross-sectional view at X-X line of FIG. 3. (Example 2)

FIG. 3 is a schematic drawing of a plan view showing other example of the specified gas concentration sensor element 100 which is the characteristic feature of the specified gas concentration sensor of the present invention, and FIG. 4 is a schematic drawing of a cross-sectional view along with the X-X thereof. Here is the case practiced by using an n-type SOI substrate as a substrate 1 similarly as in the above-mentioned Example 1, and a thin film 10 having the structure of floating in the air for heat separation from the substrate 1 is divided into two, which comprises a thin film 10a as one of the thin films and a thin film 10b as another thin film. The thin film 10a and the thin film 10b having the same shape are projected in a cantilever shape from the thin film 10, and to the thin film 10a is provided an absorbing substance 5 of the specified gas, which acts as a detection sensor, and to the other thin film 10b is formed an inactive balance film in place of the absorbing substance 5 of the specified gas, so as to have the same thermal time constant τ. Similarly as in the above-mentioned Example, temperature sensors 20 and 21 are thermocouple 120 which is a temperature difference sensor. However, a heater 25 is formed by a nichrome thin film at the common region 15 which is the root of the dividing portion thereof for heating the thin film 10a and the thin film 10b equivalently. Accordingly, the heater 25 and the temperature sensor are independent and electrically separated so that heating and measurement of the temperature can be usually measured. When the heater 25 and the thermocouple 120 are combined, they cannot be temporally operated independently, but it is suitable for the purpose of measuring the temperature at the time of heating whereas the shape is somewhat big.

The thin film 10a and the thin film 10b having the same shape are, as in Example 1, operated as the thin film 10a for the detection sensor and the thin film 10b for the reference sensor. The temperature sensors 20 and 21 mounted on these thin films are a thermocouple 120 which is a temperature difference sensor. The characteristic feature in this case is that the cold junction which is common to the temperature sensors 20 and 21 is provided to the common region 15 which is the root region at which the thin film 10a and the thin film 10b are divided from the thin film 10 and on which the heater 25 is provided, and to the n-type SOI layer 12 as the thermocouple conductor 120a is provided as an ohmic electrode 62b. Accordingly, this region is as the standard, the temperature difference of the thin film 10a and the thin film 10b generated depending on the hydrogen gas concentration can be measured as an output difference between the temperature sensors 20 and 21. Thus, as shown in Example 1, by measuring a differential output after several times of the thermal time constant τ after stopping the heating, the specified gas concentration can be measured with high precision to which the zero method is applied. In addition, the heater 25 is independently formed from the temperature sensors 20 and 21, so that when the specified gas is a hydrogen gas, there is a merit that information such as temperature rise based on burning of the hydrogen gas during heating can be easily obtained. As a matter of course, the temperature sensor mounted on the thin film 10b is heated to use as a heater, and as the heat conduction type sensor, a wide range of the hydrogen gas concentration can be also measured. In this case, a confirmation whether it is caused by a change of the heat conduction type sensor by the hydrogen is required to take in an information on the temperature change by the hydrogen gas of the thin film 10a on which the absorbing substance 5 of the hydrogen is formed.

The forming process of the specified gas concentration sensor element 100 shown in FIG. 1 and FIG. 2 are the same as the preparation of the specified gas concentration sensor element 100 in Example 1, so that the explanation is omitted here.

EXAMPLE 3

Figure 5:
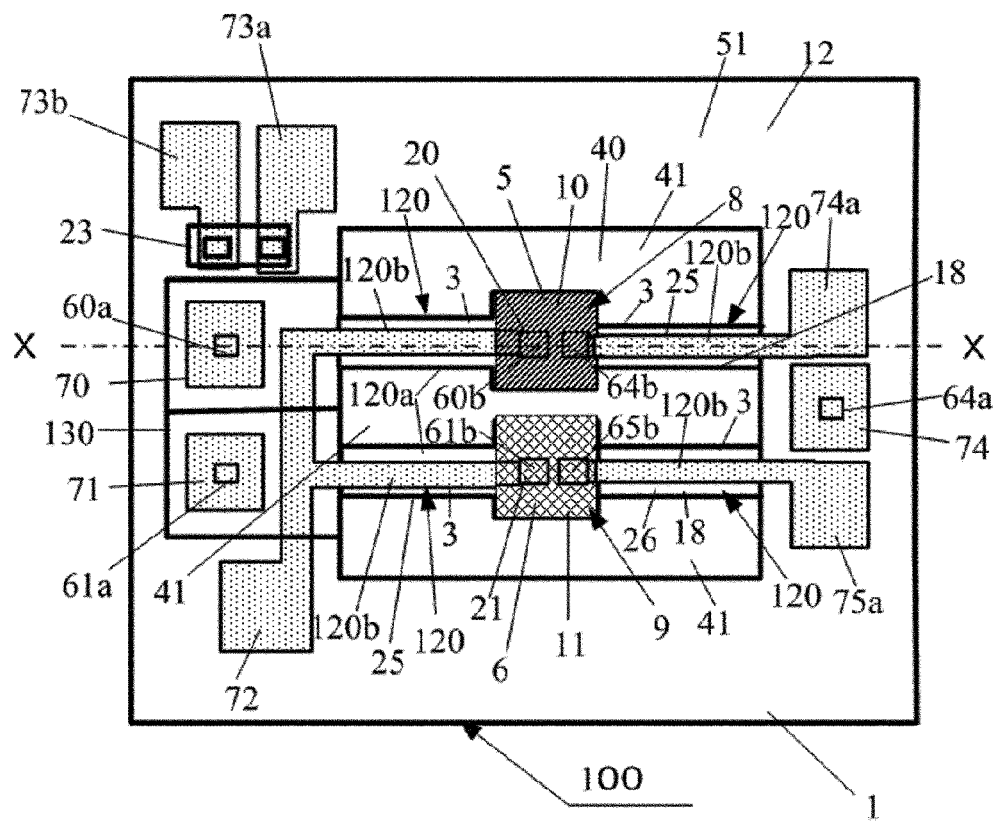
FIG. 5 This illustrates a schematic drawing of a plan view showing other example of the specified gas concentration sensor element 100 portion which is the characteristic feature of the specified gas concentration sensor of the present invention. (Example 3)
Figure 6:
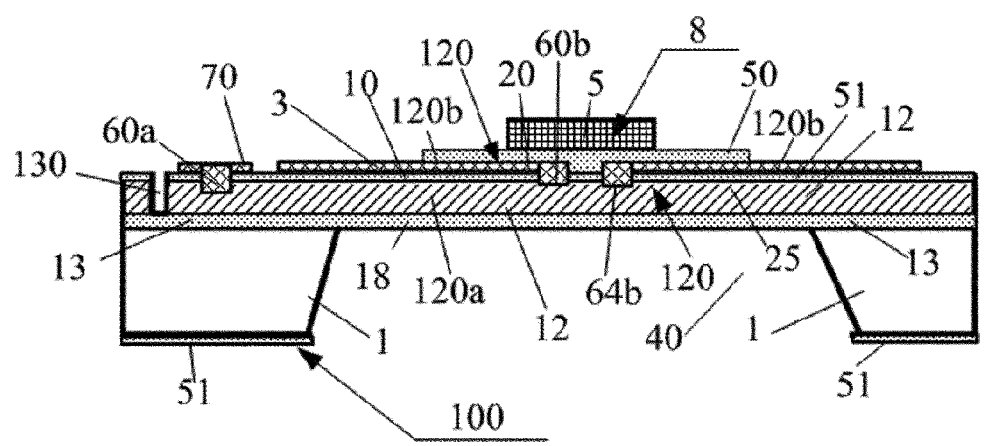
FIG. 6 This illustrates a schematic drawing of a cross-sectional view at X-X line of FIG. 5. (Example 3)

FIG. 5 is a schematic drawing of a plan view showing other example of the specified gas concentration sensor element 100 which is the characteristic feature of the specified gas concentration sensor of the present invention, and FIG. 6 is a schematic drawing of a cross-sectional view along with the X-X line thereof. A large difference from the specified gas concentration sensor element 100 shown in FIG. 1 and FIG. 2 of Example 1 is that, in FIG. 1 and FIG. 2, the thin films 10 and 11 are cantilever structures, while in FIG. 5 and FIG. 6, it is a bridge structure 3 and constituted by a crossbeam 18 which supports both ends. Moreover, to the respective thin films 10 and 11 are formed each two thermocouples 120, each one of which is utilized as temperature sensors 20 and 21 of the thermocouples which are used as the original temperature difference sensors, and each another of the thermocouples 120 is used as heaters 25 and 26. By employing such a constitution, heat conduction to the substrate 1 becomes easily large. When the specified gas is a hydrogen gas, while there is a problem that heat generation due to absorption of the hydrogen is the same, the temperature rise becomes small, but there is a merit that the response rate is quick and the strength of the thin films 10 and 11 is heightened, and further there is a merit that in the cantilever, a complicated wiring 110 can be easily taken out to the substrate 1 side since it is supported by the both ends by the bridge structure. In addition, the heater 25 and 26 as well as the temperature sensors 20 and 21 are formed to the thin films 10 and 11, respectively, so that measurement of the temperature during heating can be also carried out easily, and when the specified gas is a hydrogen gas, information during burning of the hydrogen can be easily obtained and temperature control in which the standard temperature of the temperatures of the thin films 10 and 11 is raised slightly from the room temperature can be carried out easily. The thin film 10 on which the absorbing substance 5 of the specified gas is mounted is operated as a detection sensor and the thin film 11 is operated as a reference sensor, and the measurement method of the specified gas is the same as in Example 1 so that the explanation is omitted here.

EXAMPLE 4

Figure 7:
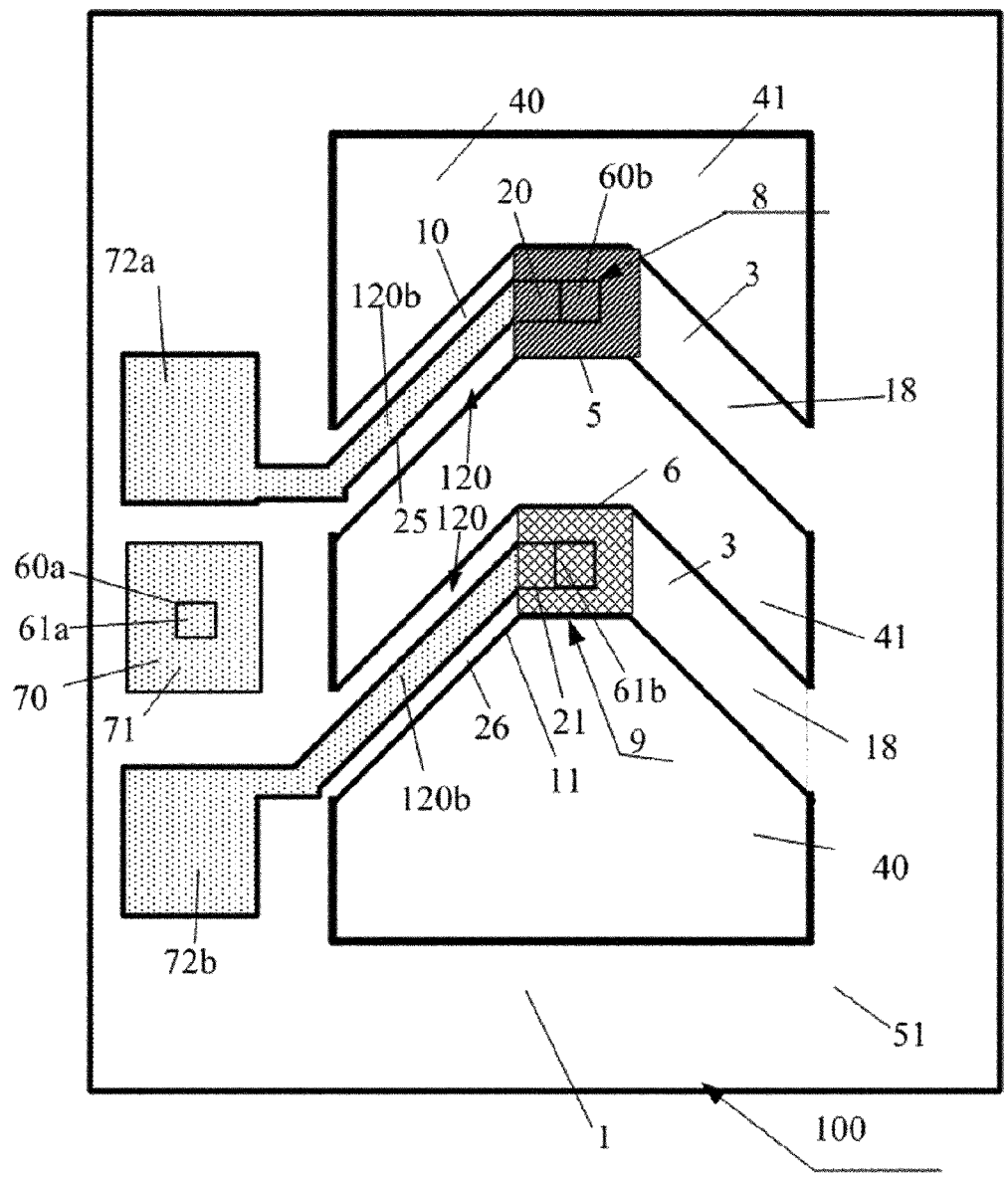
FIG. 7 This illustrates a schematic drawing of a plan view showing other example of the specified gas concentration sensor element 100 portion which is the characteristic feature of the specified gas concentration sensor of the present invention. (Example 4)

FIG. 7 is a schematic drawing of a plan view showing other example of the specified gas concentration sensor element 100 which is the characteristic feature of the specified gas concentration sensor of the present invention. For obtaining a large temperature rise even when heat generation is a little and while the thin film 10 and the thin film 11 are a bridge structure 3, it is better to make the length of the crossbeam 18 of the bridge structure 3 long. Also, when an SOI substrate comprising a silicon singlecrystalline is used as the substrate, orientation of the crystal is important for sterically processing the substrate 1 for forming a cavity 40 by an etchant using a MEMS technology. This is because the orientation of the crystal is utilized for forming a precision cavity 40 by utilizing the property that an etching rate of the (111) face of the crystal is extremely slower than the other orientation whereby etching can be stopped. For forming the crossbeam 18 with a long bridge structure 3, it is necessary to form the crossbeam 18 with a long bridge structure 3 so that the crystalline silicon is etched as in short period of time as possible in consideration with the angle and the width to the orientation of the crystal of the crossbeam 18 of the bridge structure 3.

The example herein mentioned is the case where the crossbeam 18 with a long bridge structure 3 is so formed that it has an angle of 45° to the surface of the (100) crystalline surface of the substrate and to the length direction of the cavity 40 with the (110) direction, and the crossbeam 18 with the bridge structure 3 can be considered to be like a cantilever as a whole to the supporting portion of the both ends. To the thin film 10, an absorbing substance 5 of the hydrogen is provided at the region which is a tip portion of the cantilever and a center portion of the crossbeam 18 with the bridge structure 3, and to the thin film 11, a balance film 6 such as nichrome and chromium which are inactive to the specified gas is provided in place of the absorbing substance 5 of the specified gas. The temperature sensors 20 and 21 used in this case are thermocouples 120 which are temperature difference sensors, and can be also used as the heaters 25. Incidentally, these thermocouples 120 comprise an n-type SOI layer 12 as a thermocouple conductor 120a and nichrome as a thermocouple conductor 120b. The terminal of the n-type SOI layer 12 as a thermocouple conductor 120a is commonly provided with the temperature sensors 20 and 21, and the electrode pads 70 and 71 through the ohmic electrodes 60a and 61a at the same portion correspond thereto. Accordingly, for measuring the temperature rise of the thin film 10 equipped with the absorbing substance 5 of the specified gas to be used as a detection sensor, a voltage between the electrode pad 70 and the electrode pad 72a is to be measured, and for measuring the temperature rise of the thin film 11 having no the absorbing substance 5 of the specified gas to be used as a reference sensor, a voltage between the electrode pad 71 and the electrode pad 72b is to be measured. Also, for measuring the temperature difference between the thin film 10 and the thin film 11, a voltage between the electrode pad 72a and the electrode pad 72b is to be measured. Measurement of the specified gas concentration is substantially the same as in the aforementioned example. Incidentally, in the drawing of FIG. 7, an absolute temperature sensor 23 for measuring the absolute temperature of the substrate 1 is omitted.

EXAMPLE 5

Figure 8:
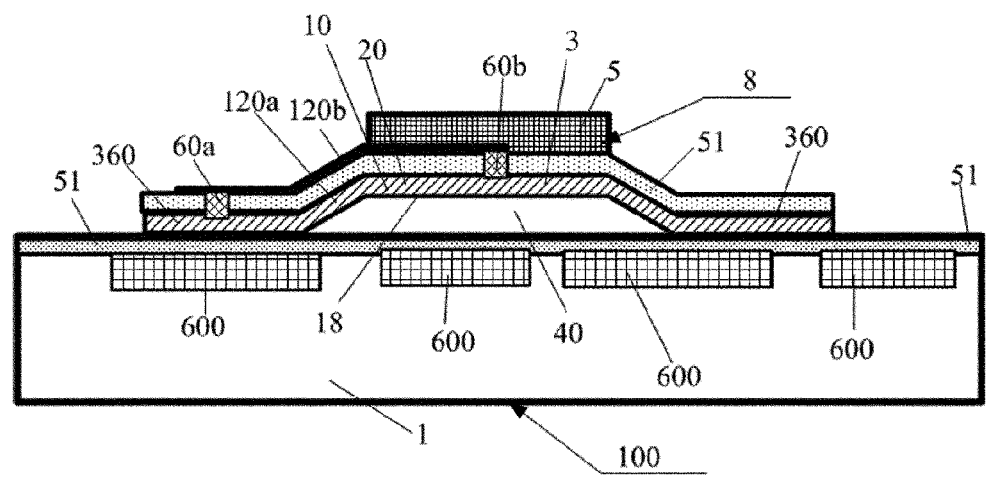
FIG. 8 This illustrates a schematic drawing of a cross-sectional view showing one example of the specified gas concentration sensor element 100 portion which is the characteristic feature of the specified gas concentration sensor of the present invention. (Example 5)

FIG. 8 is a schematic drawing of a cross-sectional view showing one example of the specified gas concentration sensor element 100 which is the characteristic feature of the specified gas concentration sensor of the present invention. In the aforementioned example, the thin film 10 and the thin film 11 provided to the specified gas concentration sensor element 100 are thermally separated from the substrate 1 by sterically processing the substrate 1 itself such as silicon, etc., to have a cavity 40 at the bottom portion. The example herein mentioned is to intend to thermal separation from the substrate 1 by forming a thin film which becomes a cantilever or a crossbeam 8 of the bridge structure overlaying a sacrificing layer (this is not shown here. It was embedded at the portion of the cavity 40 but removed by etching at the time of forming the cavity), then, removing the sacrificing layer by etching to form the cavity 40 portion, and forming the thin film 10 and the thin film 11 to the cantilever 7 shape or the bridge structure 3. When such a thin film 10 and a thin film 11 are to be formed on the substrate 1, various kinds of IC electronic circuits such as an OP amplifier, a driving circuit for the heaters 25 and 26, an arithmetic circuit, a memory circuit, a control circuit and an indicating circuit for operating as the specified gas concentration sensor are previously formed on the substrate at the lower portion, and then, the thin film 10 and the thin film 11 are formed. By preparing the material as mentioned above, the shape of the specified gas concentration sensor becomes compact and a specified gas concentration sensor integrated by the electronic circuits can be provided. When a polysilicon is used as the main material of the thin film 10 and the thin film 11, it is suitable since the heaters 25 and 26 and the thermocouple 120 are easily formed. In the example shown in FIG. 8, a structural material is shown wherein the thin film 10 and the thin film 11 are formed by the n-type low resistance polysilicon thin film, a cavity 40 is formed as a result of etching a sacrificing layer, and they are fixed to the silicon singlecrystalline substrate 1 at an anchor portion 360 to make a thermally separated state from the substrate 1 on its own. As the absorbing substance 5 of the specified gas, for example, palladium Pd is used for the hydrogen gas and titanium disulfide is used for the oxygen gas, and these can be formed by sputtering in the same manner as in the aforementioned examples. The operation is the same as in the aforementioned examples which use the thin film 10 and the thin film 11 formed by processing the substrate 1 itself.

EXAMPLE 6

Figure 9:
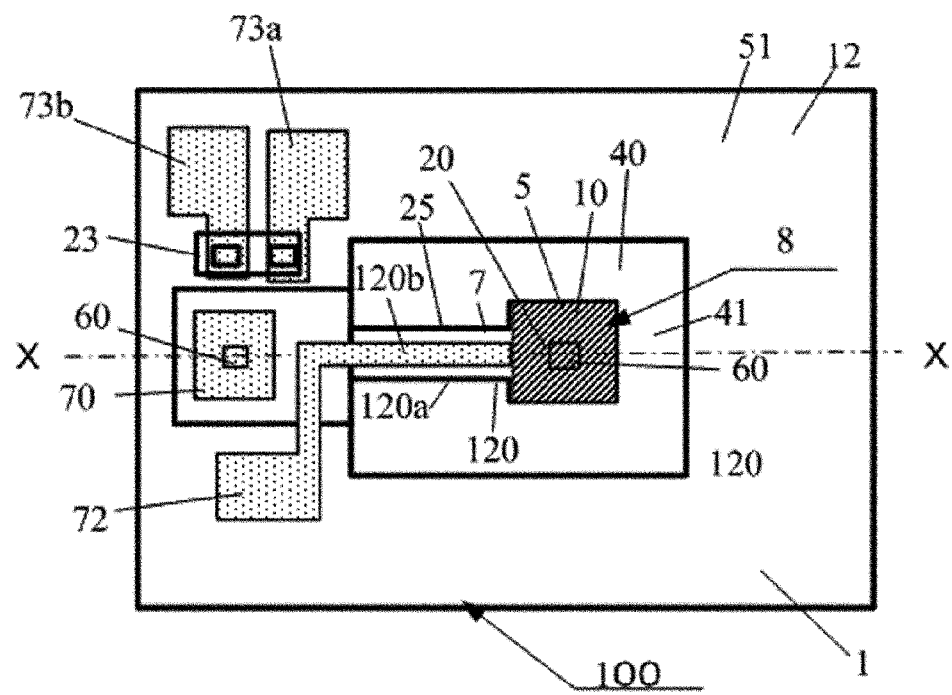
FIG. 9 This illustrates a schematic drawing of a plan view showing other example of the specified gas concentration sensor element 100 portion which is the characteristic feature of the specified gas concentration sensor of the present invention. (Example 6)

The shape of the above-mentioned specified gas concentration sensor is mainly shown in the case of the shape where the specified gas is a hydrogen gas. However, in the case of the hydrogen gas sensor, when it has been known that it is the case of the peak hydrogen gas concentration or less utilizing a heat generation effect of absorption (storage) of the hydrogen, the thin film 11 which is a reference sensor in FIG. 1 is not necessary as mentioned above. When the specified gas is, for example, an oxygen gas, a heat generation effect based on intercalation of titanium disulfide which is the absorbing substance 5 of the oxygen is monotonic increase from the oxygen concentration of 0 to 100% so that the thin film 11 which is a reference sensor in FIG. 1 is not necessary. FIG. 9 shows the case where it is a simple structure in which the thin film 11 as a reference sensor of FIG. 1 is omitted. For example, when it is used as an oxygen gas concentration sensor, a layered crystalline thin film of titanium disulfide which is the absorbing substance 5 of the oxygen is formed to the thin film 10 as a detection sensor 8, and an amount of the temperature rise of the substrate 1 based on the absorption-heat generation effect when the oxygen is absorbed by the absorbing substance 5 of the oxygen by intercalation is measured. Absorption of the oxygen depends on the temperature of the absorbing substance 5, and when the temperature is high, an absorption amount is a little and the heat generation amount is also a little. Also, when the oxygen is sufficiently absorbed and not absorbed any more, the heat generation is stopped and it is returned to room temperature as the circumferential temperature. The temperature rise to the substrate 1 at this time can be measured by using a thermocouple 120 which is a temperature sensor 20 as the temperature difference sensor. Thus, without the thin film 11 as a reference sensor, by heating the detection sensor 8 with the heater 25 (in this case, the thermocouple 120 and the heater 25 are used in combination) to release the oxygen gas which had been absorbed, and measuring the temperature rise from the substrate 1 at a specific time (several times of the thermal time constant τ of the cantilever 7 of the original detection sensor 8) or later during the cooling procedure after stopping the heating by the thermocouple 120, the oxygen concentration can be measured.

When the ambient gas is, for example, an air in which the oxygen has been already in a certain equilibrium state, the oxygen concentration can be measured with the equilibrium state as the standard. That is, in the air, the nitrogen gas and the oxygen gas are present with a ratio of 4:1, and when the thin film 10 as the detection sensor 8 is heated from the room temperature, an oxygen gas is released and when the heating is stopped, the absorbing substance 5 is starting to absorb the oxygen to generate heat but it will return to room temperature any more so that it becomes a thermally equilibrium state at the oxygen concentration in the air and heat generation quits. This heat generation amount is a different value from the case where calibration is carried out in the state where no oxygen is present in the ambient gas. Thus, at the time of calibration of the absolute oxygen gas concentration, it is necessary to previously obtain and prepare the characteristic data for calibration. For example, it will be better to prepare calibration data using a standard gas with the oxygen absolute concentration in a pure nitrogen gas.

EXAMPLE 7

Figure 10:
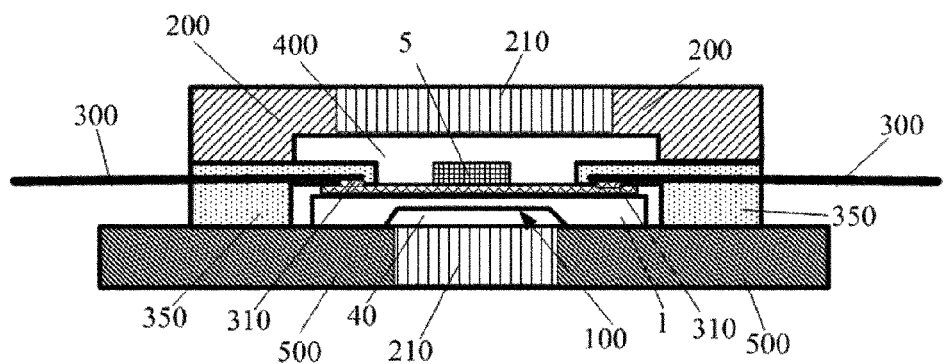
FIG. 10 This illustrates a schematic drawing of a cross-sectional view showing one example of the specified gas concentration sensor package in which the specified gas concentration sensor of the present invention is made an explosion-proof type, and the specified gas is made a hydrogen gas. (Example 7)

FIG. 10 is a schematic drawing of a cross-sectional view showing one example of the specified gas concentration sensor package which is made an explosion-proof type to the combustible gas such as a hydrogen gas by covering the specified gas concentration sensor element 100 which is the characteristic feature of the specified gas concentration sensor of the present invention with a cap having a mesh structure to shut out the air stream. The specified gas concentration sensor element 100 is connected to an element holder 500 comprising an alumina substrate or a flame retardant plastic substrate, an electrically insulating lead holder 350 provided by a lead 300 is connected and the lead 300 and each electrode pad of the specified gas concentration sensor element 100 are electrically connected through a lead connecting portion 310. Also, power supply as well as input and output of electric signals between the outside and the specified gas concentration sensor element 100 are carried out through the lead 300. Moreover, a cap 200 having a mesh structure is connected so that the porous mesh structure portion 210 is located at around a cavity 40 portion at which the thin film 10 and the thin film 11 of the specified gas concentration sensor element 100 are provided. Also, it is more effective if the mesh structure portion 210 at the element holder 500 depending on necessity. In this example, it is shown the case where the mesh structure portion 210 is provided also at the element holder 500.

EXAMPLE 8

Figure 11:
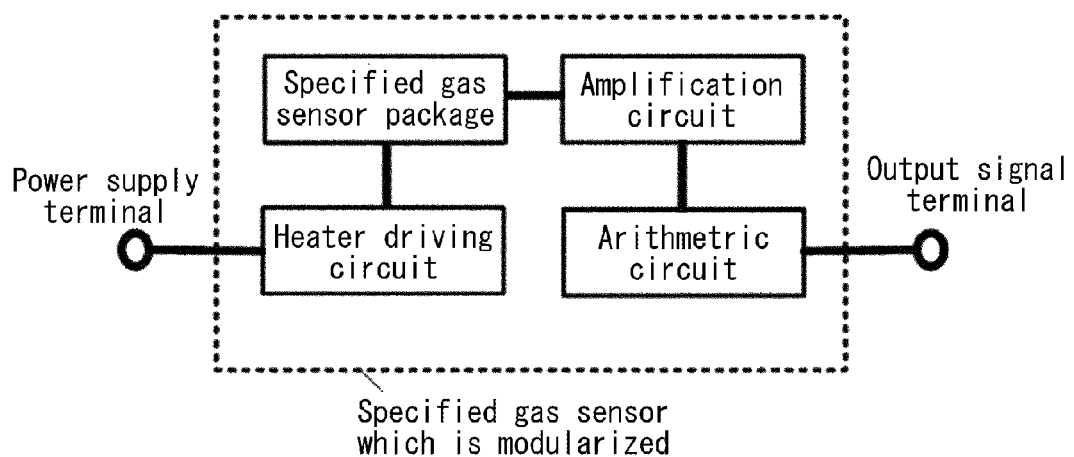
FIG. 11 This illustrates a block diagram showing one example of the specified gas concentration sensor of the present invention. (Example 8)

FIG. 11 is a block diagram showing other example of the specified gas concentration sensor of the present invention, and this is the case where the specified gas concentration sensor package in which the characteristic specified gas concentration sensor element 100 is incorporated and an electronic circuit are integrated and modularized. In this example, a heater driving circuit, an amplification circuit and an arithmetic circuit are used as the electronic circuit. Here is the case where power supply is taken from the outside, and further an output signal terminal is provided so that the signal relating to the specified gas concentration can be taken out to the outside.

EXAMPLE 9

Figure 12:
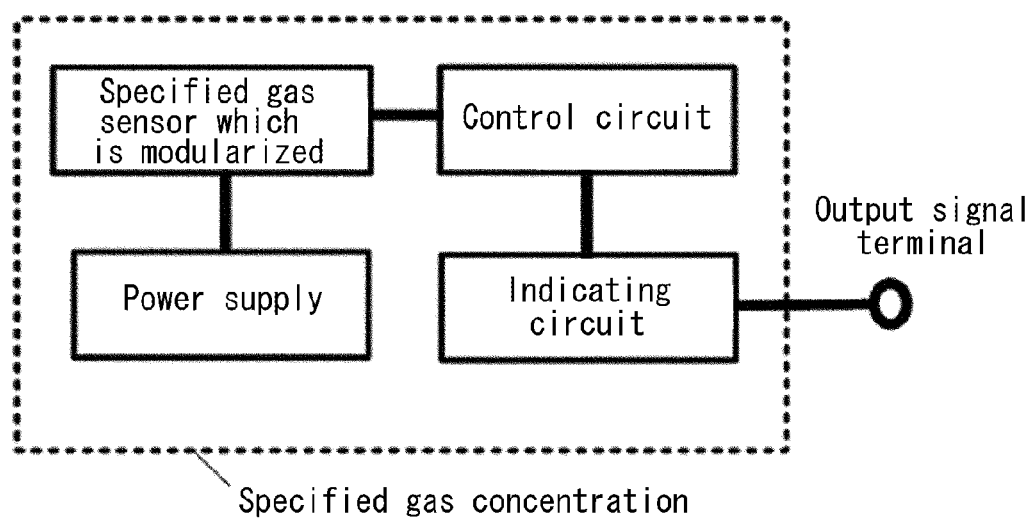
FIG. 12 This illustrates a block diagram showing other example of the specified gas concentration sensor of the present invention. (Example 9)
Figure 13:
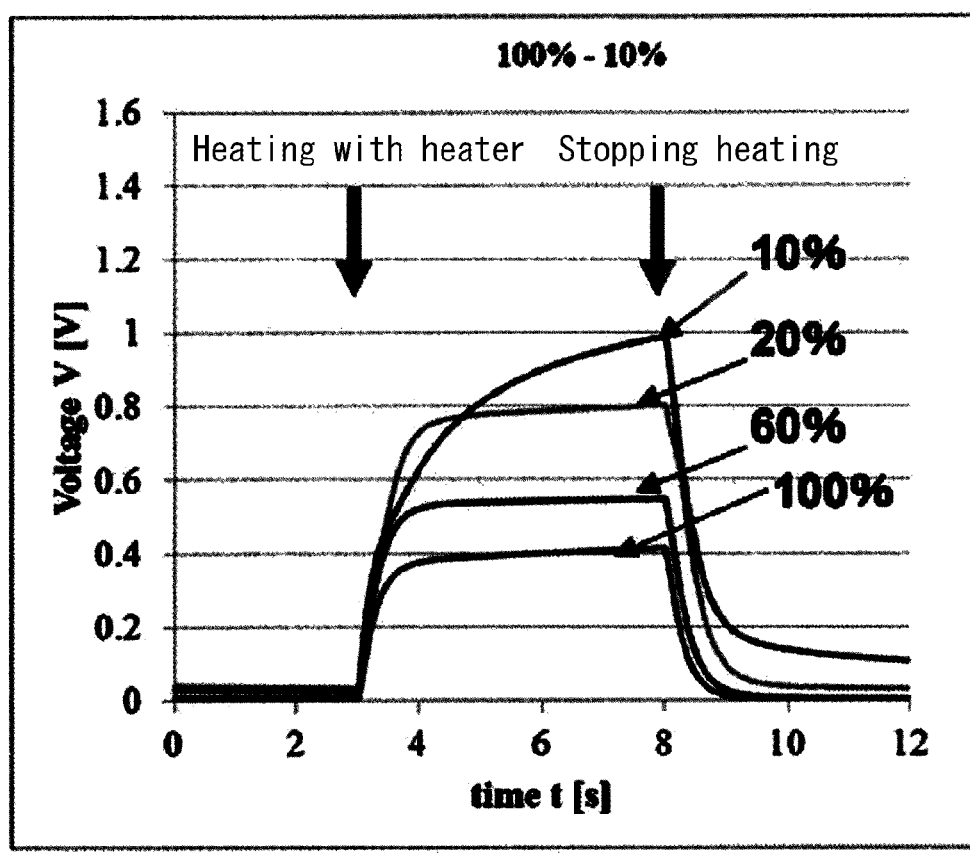
FIG. 13 This illustrates an output characteristic of the experimental data at the time of heating with the heater in the region in which a hydrogen gas concentration as the specified gas is large of the experimentally produced specified gas concentration sensor.
Figure 14:
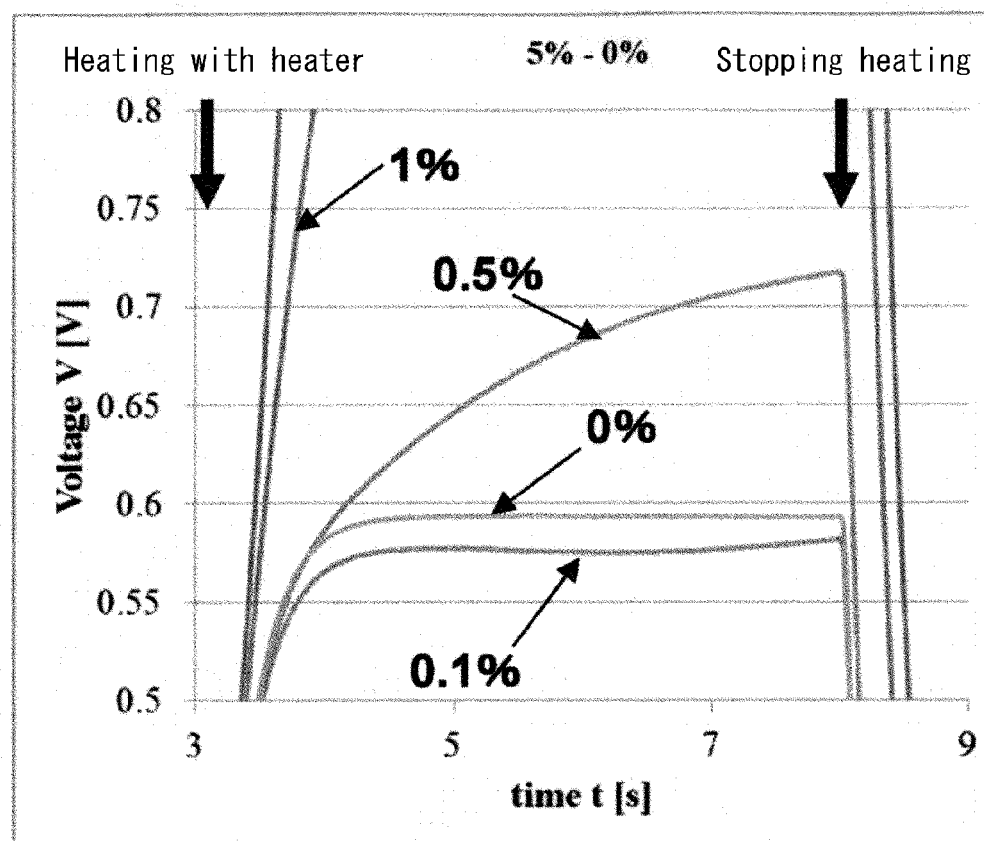
FIG. 14 This illustrates an output characteristic of the experimental data at the time of heating with the heater in the region in which a hydrogen gas concentration as the specified gas is a little of the experimentally produced specified gas concentration sensor.
Figure 15:
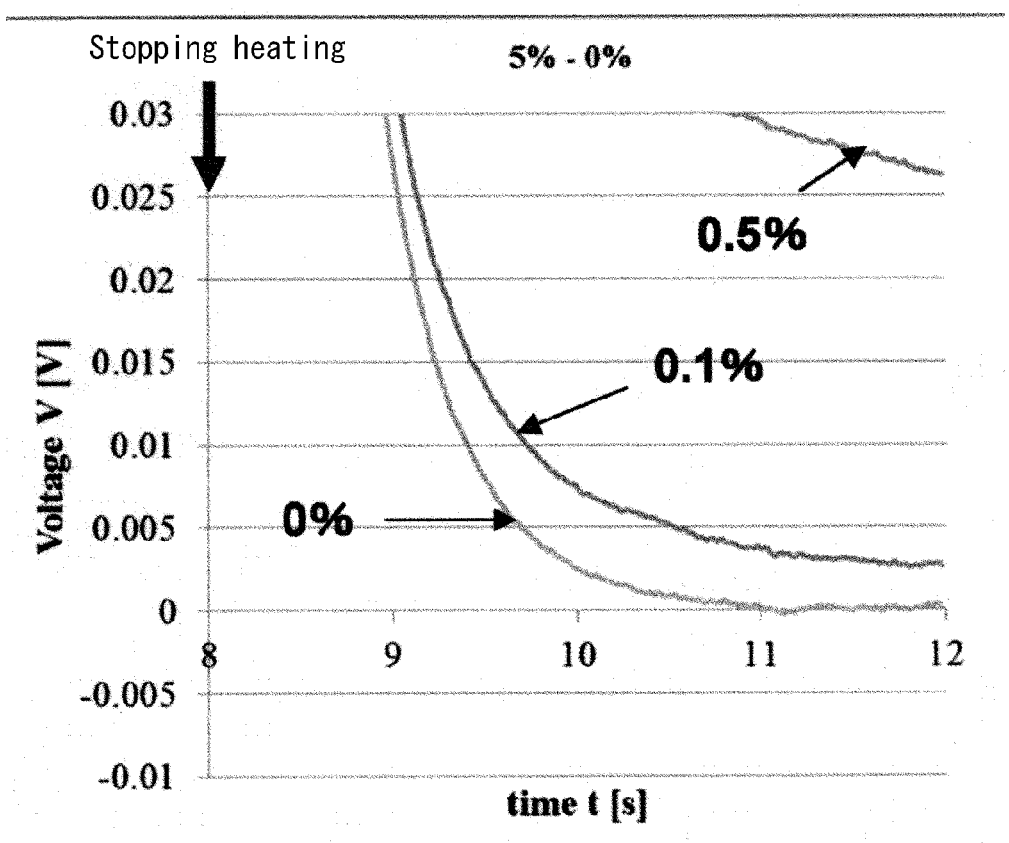
FIG. 15 This illustrates an output characteristic of the experimental data in the cooling procedure in the region in which a hydrogen gas concentration as the specified gas is a little of the experimentally produced specified gas concentration sensor.
Figure 16:
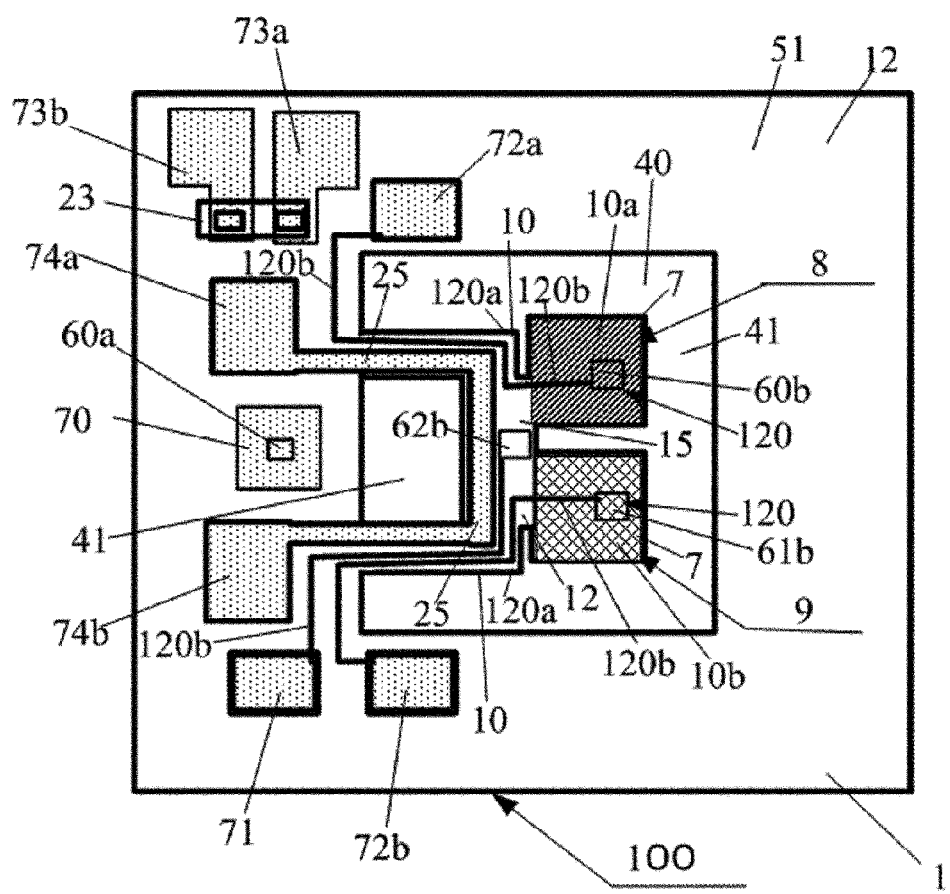
FIG. 16 This illustrates a schematic drawing of a cross-sectional view showing other one example (initial stage structure) of the specified gas concentration sensor element 100 portion which is the characteristic feature of the specified gas concentration sensor of the present invention.

FIG. 12 is a block diagram showing other example of the specified gas concentration sensor of the present invention, and it is a specified gas concentration sensor which can be further provided as a specified gas concentration meter using a specified gas concentration sensor in which the specified gas concentration sensor package shown in Example 7 and an electronic circuit are integrated and modularized, which device is prepared by incorporating a power supply, a control circuit and an indicating circuit which can display the hydrogen gas concentration, etc. Moreover, this is the case where an output signal terminal is also provided so that the signal of the specified gas concentration can be output to the outside. The specified gas concentration meter can be, of course, a hydrogen gas concentration meter when the hydrogen gas is objected to as the specified gas, and can be an oxygen gas concentration meter when the oxygen gas is objected to as the specified gas.

The above-mentioned was a specified gas concentration sensor element in the case of using an n-type SOI layer 12, but the same sensor can be accomplished when a p-type SOI layer 12 is utilized as a matter of course.

The specified gas concentration sensor of the present invention is not limited by the above-mentioned Examples, and, of course, various variations can be present while the gist, the action and the effect of the present invention are the same.

Utilizability in Industry

The specified gas concentration sensor of the present invention is a thermal type sensor for measuring the temperature rise by the exothermic reaction due to absorption by the absorbing substance 5 of the specified gas with high sensitivity and high precision. For example, when the specified gas concentration sensor of the present invention is applied to measure the concentration of a specified gas in the air, if an extremely small-sized thermocouple which can detect a temperature difference alone with high sensitivity and high precision is used to a thin film floating in the air, the zero method can be applied so that, in particular, when the specified gas is a hydrogen gas, a hydrogen gas concentration of 4% or less which is an explosion limit in the air can be measured with extremely high precision. Also, when the specified gas is an oxygen gas, the oxygen gas has a thermal conductivity substantially the same as that of the air and a heat generation amount increases substantially monotonously depending on the oxygen concentration so that an oxygen gas concentration from 0 to 100% can be simply measured by utilizing heat generation by absorption of the oxygen gas. However, in the case of the hydrogen gas, the hydrogen gas is a gas having the highest thermal conductivity, so that an effect (it has a peak at the hydrogen concentration (about 5% or so) which causes temperature rise due to heat generation by absorption) derived from large thermal conductivity of the hydrogen gas at a certain hydrogen concentration or higher comes to the surface. Due to this effect, the hydrogen gas concentration from 0 to 100% can be measured by using an operation as a heat conduction type sensor which utilizes the fact that the thermal conductivity becomes large as the hydrogen gas amount in the hydrogen gas atmosphere becomes large which is a different mechanism from the detection mechanism based on heat generation by absorption of the hydrogen, by using a reference sensor having no absorption substance 5 of the hydrogen, or by using a reference sensor in which the surface of the absorbing substance 5 is inactivated, etc.

The invention claimed is:

1. A specified gas concentration sensor which comprises:
a substrate;
a thin film thermally separated from the substrate;
a heater comprising part of the thin film;
a temperature sensor comprising part of the thin film;
an absorbing substance of a specified gas comprising part of the thin film, temperature change accompanied by heat generation at a time of absorbing the specified gas in an ambient gas being capable of measuring by the temperature sensor; and a control circuit,
wherein the control circuit is configured so that the absorbed specified gas is released from the absorbing substance in a heating cycle by heating with the heater, and in a cooling cycle after stopping heating with the heater, at a time frame in which cooling is substantially finished when the specified gas concentration is 0%, the specified gas once released from the absorbing substance by heating is getting to be absorbed and a temperature rise occurs based on an exothermic reaction at a time of absorbing the specified gas and a thermal time constant $\tau$ that tends to become large is utilized, and after stopping heating with the heater, the specified gas concentration in the ambient gas is obtained by utilizing an output of the temperature sensor at a time passing a predetermined time which at least exceeds the thermal time constant $\tau$ of the thin film or longer at which the specified gas is not present at the heater, and that will repeat these heating and cooling cycles.

2. The specified gas concentration sensor according to claim 1, wherein the specified gas is a hydrogen gas.

3. The specified gas concentration sensor according to claim 2, wherein the absorbing substance of hydrogen is a substance containing platinum (Pt) or palladium (Pd) which is a chemically stable substance.

4. The specified gas concentration sensor according to claim 3, wherein a temperature of the temperature sensor is measured by heating the heater with a predetermined electric power, voltage or electric current, after stopping, at a time passing a predetermined time of the thermal time constant $\tau$ of the thin film or longer during a cooling procedure, and the hydrogen gas concentration is obtained in a hydrogen gas concentration range of a peak hydrogen gas concentration or lower.

5. The specified gas concentration sensor according to claim 2, wherein the absorbing substance is coated by a protective film so that a gas different from hydrogen which physically or chemically reacts with the absorbing substance of the hydrogen is not directly contacted with the absorbing substance.

6. The specified gas concentration sensor according to claim 5, wherein a temperature of the temperature sensor is measured by heating the heater with a predetermined electric power, voltage or electric current, after stopping, at a time passing a predetermined time of the thermal time constant $\tau$ of the thin film or longer during a cooling procedure, and the hydrogen gas concentration is obtained in a hydrogen gas concentration range of a peak hydrogen gas concentration or lower.

7. The specified gas concentration sensor according to claim 2, wherein a temperature of the temperature sensor is measured by heating the heater with a predetermined electric power, voltage or electric current, after stopping, at a time passing a predetermined time of the thermal time constant $\tau$ of the thin film or longer during a cooling procedure, and the hydrogen gas concentration is obtained in a hydrogen gas concentration range of a peak hydrogen gas concentration or lower.

8. The specified gas concentration sensor according to claim 2, wherein the thin film is a first thin film, and a second thin film different from the first thin film is provided thermally separated from the substrate, and the second thin film further comprises a heater and a temperature sensor and an absorbing substance of hydrogen is not provided or a balance film inactive as an absorbing substance is provided on the second thin film, the heater is heated under a predetermined electric power, voltage or electric current, measurement of the temperature of the heater during heating or the temperature after passing a predetermined time during cooling from immediately after stopping the heating, or measurement of a passed time until the temperature becomes a predetermined one is carried out by using the temperature sensor, and the concentration of the hydrogen gas from 3% to 100% can be measured by utilizing an output or change in the output of the temperature based on the difference in thermal conductivity depending on the hydrogen gas concentration in the ambient gas.

9. The specified gas concentration sensor according to claim 8, wherein the second thin film is separately formed from the first thin film, which is thermally separated from the substrate, and made an equal shape of the first thin film without having the absorbing substance of the specified gas.

10. The specified gas concentration sensor according to claim 8, wherein the temperature sensors are temperature difference sensors.

11. The specified gas concentration sensor according to claim 8, wherein an electric current is applied to the temperature sensors to use the temperature sensors as the heaters.

12. The specified gas concentration sensor according to claim 2, wherein for estimating a rough range of the hydrogen gas concentration in an ambient gas, output information of the temperature sensor based on burning of the hydrogen during heating with the heater can be utilized by heating the heater under a predetermined electric power, voltage or electric current.

13. The specified gas concentration sensor according to claim 1, wherein the specified gas is an oxygen gas.

14. The specified gas concentration sensor according to claim 13, wherein a layered substance is contained in an absorbing substance of the oxygen, and an exothermic reaction accompanied by an intercalation reaction of the oxygen at the layered substance is utilized.

15. The specified gas concentration sensor according to claim 1, wherein the thin film is divided into at least two thin films including a first thin film and a second thin film, the heater which can equally heat the first thin film and the second thin film is provided at a common region of a part near the root at which the first thin film and the second thin film are divided, the temperature sensor and the absorbing substance of the specified gas are provided to the first thin film, a temperature sensor is provided to the second thin film, an absorbing substance of the specified gas is not provided or the balance film inactive as an absorbing substance is provided on the second thin film, the first thin film is used as a sensor for detecting the specified gas, the second thin film is treated as a reference sensor, and the temperature difference between the first thin film and the second thin film can be detected and output information of the temperature difference can be utilized.

16. The specified gas concentration sensor according to claim 15, wherein the first thin film and the second thin film are substantially the same shape, and depending on necessity, a substance having the same heat capacity as the absorbing substance of the specified gas formed at the first thin film is formed to the second thin film as a balance film.

17. The specified gas concentration sensor according to claim 15, wherein the temperature sensors are temperature difference sensors.

18. The specified gas concentration sensor according to claim 15, wherein an electric current is applied to the temperature sensors to use the temperature sensors as the heaters.

19. The specified gas concentration sensor according to claim 1, wherein an absolute temperature sensor is provided at the substrate for measurement of the temperature of the ambient gas.

20. The specified gas concentration sensor according to claim 1, wherein the substrate (1) is a semiconductor substrate, the thin film is formed through a sacrificing layer which has been formed by overlaying upward of the substrate, the sacrificing layer is removed by etching to form a cavity, and an electronic circuit can be formed to the substrate.

21. The specified gas concentration sensor according to claim 1, wherein the specified gas concentration sensor is covered by a cap having a mesh structure to shut out air stream.

22. The specified gas concentration sensor according to claim 1, wherein at least an electronic circuit is provided so that the heater is heated with a predetermined cycle, and the specified gas concentration in the ambient gas is measured and a measured concentration can be taken out to an outside.

23. The specified gas concentration sensor according to claim 1, wherein the thin film comprises a cantilever structure or a bridge structure.

* * * * *